(12) United States Patent
Hanson et al.

(10) Patent No.: US 9,370,621 B2
(45) Date of Patent: Jun. 21, 2016

(54) NEEDLE INSERTION SYSTEMS AND METHODS

(75) Inventors: Ian B. Hanson, Northridge, CA (US); Julian D. Kavazov, Arcadia, CA (US); Rafael Bikovsky, Oak Park, CA (US)

(73) Assignee: MEDTRONIC MINIMED, INC., Northridge, CA (US)

( * ) Notice: Subject to any disclaimer, the term of this patent is extended or adjusted under 35 U.S.C. 154(b) by 670 days.

(21) Appl. No.: 12/336,367

(22) Filed: Dec. 16, 2008

(65) Prior Publication Data
US 2010/0152658 A1  Jun. 17, 2010

(51) Int. Cl.
*A61M 5/20* (2006.01)
*A61M 5/158* (2006.01)
*A61M 5/142* (2006.01)
(Continued)

(52) U.S. Cl.
CPC .......... *A61M 5/2033* (2013.01); *A61M 5/14248* (2013.01); *A61M 5/1413* (2013.01); *A61M 5/3287* (2013.01); *A61M 2005/1426* (2013.01); *A61M 2005/14252* (2013.01); *A61M 2005/1581* (2013.01); *A61M 2005/1585* (2013.01); *A61M 2005/2073* (2013.01); *A61M 2205/58* (2013.01); *A61M 2205/583* (2013.01); *A61M 2205/585* (2013.01); *A61M 2205/586* (2013.01); *Y10T 29/49826* (2015.01)

(58) Field of Classification Search
CPC ............ A61M 5/204; A61M 5/31511; A61M 5/3287; A61M 5/2033; A61M 2005/202; A61M 2005/2026; A61M 2005/206; A61M 2005/2073; A61M 2039/1016

USPC ............ 604/164.01, 164.07, 164.08, 164.12, 604/194–196
See application file for complete search history.

(56) References Cited

U.S. PATENT DOCUMENTS

| 2,856,924 | A | * | 10/1958 | Rockwell et al. | .............. 604/136 |
| 3,712,301 | A | * | 1/1973 | Sarnoff | .......................... 604/136 |
| 3,986,508 | A |  | 10/1976 | Barrington | |

(Continued)

FOREIGN PATENT DOCUMENTS

| WO | WO 01/70307 A1 | 9/2001 |
| WO | WO-02/02165 A2 | 1/2002 |

(Continued)

OTHER PUBLICATIONS

Invitation to Pay Additional Fees and Partial International Search Report for PCT No. PCT/US2009/067846 dated Mar. 29, 2010.

(Continued)

*Primary Examiner* — Theodore Stigell
*Assistant Examiner* — Benjamin Koo
(74) *Attorney, Agent, or Firm* — Foley & Lardner LLP

(57) ABSTRACT

A housing may have a needle, plunger, and bias mechanism supported within the housing by a tab configured to retain the plunger in position and to allow the plunger to move under bias force imparted by the bias mechanism to move the needle to an insert position when the tab is removed. A base and a structure may be configured for relative movement there between and may be adapted to be secured to a user with a cannula extending through a body of the structure into the user during use of a medical device. A housing may be adapted to be secured to a user to support a medical device operable with an insertion needle, the housing having a magnifying material for increasing visibility of an injection site.

47 Claims, 20 Drawing Sheets

(51) Int. Cl.
*A61M 5/14* (2006.01)
*A61M 5/32* (2006.01)

(56) References Cited

U.S. PATENT DOCUMENTS

| | | | |
|---|---|---|---|
| 4,755,173 | A | 7/1988 | Konopka et al. |
| 5,098,397 | A | 3/1992 | Svensson et al. |
| 5,176,662 | A | 1/1993 | Bartholomew et al. |
| 5,848,990 | A | 12/1998 | Cirelli et al. |
| 5,858,990 | A | 1/1999 | Walsh |
| 5,957,927 | A | 9/1999 | Magee et al. |
| 6,088,608 | A | 7/2000 | Schulman et al. |
| 6,119,028 | A | 9/2000 | Schulman et al. |
| 6,443,928 | B1 | 9/2002 | Francis |
| 6,589,229 | B1 | 7/2003 | Connelly et al. |
| 6,685,674 | B2 | 2/2004 | Douglas et al. |
| 6,740,072 | B2 | 5/2004 | Starkweather et al. |
| 6,827,702 | B2 | 12/2004 | Lebel et al. |
| 6,991,619 | B2 | 1/2006 | Marano-Ford et al. |
| 7,014,625 | B2 | 3/2006 | Bengtsson |
| 7,318,816 | B2 | 1/2008 | Bobroff et al. |
| 7,323,142 | B2 | 1/2008 | Pendo et al. |
| 7,407,493 | B2 | 8/2008 | Cane' |
| 7,455,663 | B2 | 11/2008 | Bikovsky |
| 7,585,287 | B2 | 9/2009 | Bresina et al. |
| 7,935,096 | B2 | 5/2011 | Johansson et al. |
| 8,187,232 | B2 | 5/2012 | Chong et al. |
| 8,303,549 | B2 | 11/2012 | Mejlhede et al. |
| 8,647,304 | B2 | 2/2014 | Axelsson et al. |
| 8,992,474 | B2 | 3/2015 | Hanson et al. |
| 2001/0041869 | A1 | 11/2001 | Causey, III et al. |
| 2002/0022855 | A1 | 2/2002 | Bobroff et al. |
| 2002/0055711 | A1* | 5/2002 | Lavi et al. ............ 604/110 |
| 2003/0176813 | A1 | 9/2003 | Mathias et al. |
| 2003/0176852 | A1 | 9/2003 | Lynch et al. |
| 2003/0212364 | A1 | 11/2003 | Mann et al. |
| 2004/0010207 | A1 | 1/2004 | Flaherty et al. |
| 2004/0073095 | A1 | 4/2004 | Causey, III et al. |
| 2004/0073169 | A1* | 4/2004 | Amisar et al. ......... 604/141 |
| 2004/0158207 | A1* | 8/2004 | Hunn et al. ........... 604/164.01 |
| 2005/0065760 | A1 | 3/2005 | Murtfeldt et al. |
| 2006/0095014 | A1 | 5/2006 | Ethelfeld |
| 2006/0157971 | A1 | 7/2006 | Baldwin et al. |
| 2006/0253085 | A1 | 11/2006 | Geismar et al. |
| 2006/0264894 | A1 | 11/2006 | Moberg et al. |
| 2006/0276770 | A1 | 12/2006 | Rogers |
| 2007/0161909 | A1 | 7/2007 | Goldman et al. |
| 2008/0051697 | A1 | 2/2008 | Mounce et al. |
| 2008/0051698 | A1 | 2/2008 | Mounce et al. |
| 2008/0051709 | A1 | 2/2008 | Mounce et al. |
| 2008/0051710 | A1 | 2/2008 | Moberg et al. |
| 2008/0051711 | A1 | 2/2008 | Mounce et al. |
| 2008/0051714 | A1 | 2/2008 | Moberg et al. |
| 2008/0051716 | A1 | 2/2008 | Stutz |
| 2008/0051718 | A1 | 2/2008 | Kavazov et al. |
| 2008/0051727 | A1 | 2/2008 | Moberg et al. |
| 2008/0051738 | A1 | 2/2008 | Griffin |
| 2008/0051765 | A1 | 2/2008 | Mounce |
| 2008/0077081 | A1 | 3/2008 | Mounce et al. |
| 2008/0097291 | A1 | 4/2008 | Hanson et al. |
| 2008/0097321 | A1 | 4/2008 | Mounce et al. |
| 2008/0097326 | A1 | 4/2008 | Moberg et al. |
| 2008/0097327 | A1 | 4/2008 | Bente et al. |
| 2008/0097328 | A1 | 4/2008 | Moberg et al. |
| 2008/0097375 | A1 | 4/2008 | Bikovsky |
| 2008/0097381 | A1 | 4/2008 | Moberg et al. |
| 2008/0269687 | A1 | 10/2008 | Chong et al. |
| 2008/0281270 | A1 | 11/2008 | Cross et al. |
| 2009/0012472 | A1 | 1/2009 | Ahm et al. |
| 2010/0152674 | A1* | 6/2010 | Kavazov et al. ......... 604/218 |
| 2010/0312197 | A1* | 12/2010 | Sano et al. ............ 604/220 |
| 2011/0046456 | A1 | 2/2011 | Hordum et al. |

FOREIGN PATENT DOCUMENTS

| | | | |
|---|---|---|---|
| WO | WO 2004/030716 A2 | 4/2004 | |
| WO | WO 2004/030717 A2 | 4/2004 | |
| WO | WO 2007/032352 * | 3/2007 | ............ A61M 5/315 |
| WO | WO-2008/024810 A2 | 2/2008 | |
| WO | WO-2008/065646 A1 | 6/2008 | |
| WO | WO-2008/133702 A1 | 11/2008 | |

OTHER PUBLICATIONS

Search Report dated Jun. 18, 2010 from related PCT application No. PCT/US2009/067846.
US Notice of Allowance for U.S. Appl. No. 12/894,284 DTD Apr. 2, 2012.
US Office Action dated Jul. 8, 2011 from related U.S. Appl. No. 12/894,284.
U.S. Notice of Allowance dated Dec. 3, 2014, from related U.S. Appl. No. 12/948,342.
US Office Action on U.S. Appl. No. 12/948,326 DTD Mar. 7, 2012 (10 pages).
US Office Action on U.S. Appl. No. 12/948,326 DTD Aug. 29, 2012 (10 pages).
US Office Action on U.S. Appl. No. 12/948,326 DTD Jul. 6, 2015 (9 pages).
US Office Action dated Dec. 15, 2015, from related U.S. Appl. No. 12/948,326.
Interview Summary dated Mar. 17, 2016, for U.S. Appl. No. 12/948,326.
US Notice of Allowance dated Mar. 30, 2016, for U.S. Appl. No. 12/948,326.
US Office Action dated Aug. 18, 2011, from related U.S. Appl. No. 12/948,342.
US Office Action dated Nov. 25, 2011, from related U.S. Appl. No. 12/948,342.
US Office Action dated Oct. 27, 2011, from related U.S. Appl. No. 12/894,284.

* cited by examiner

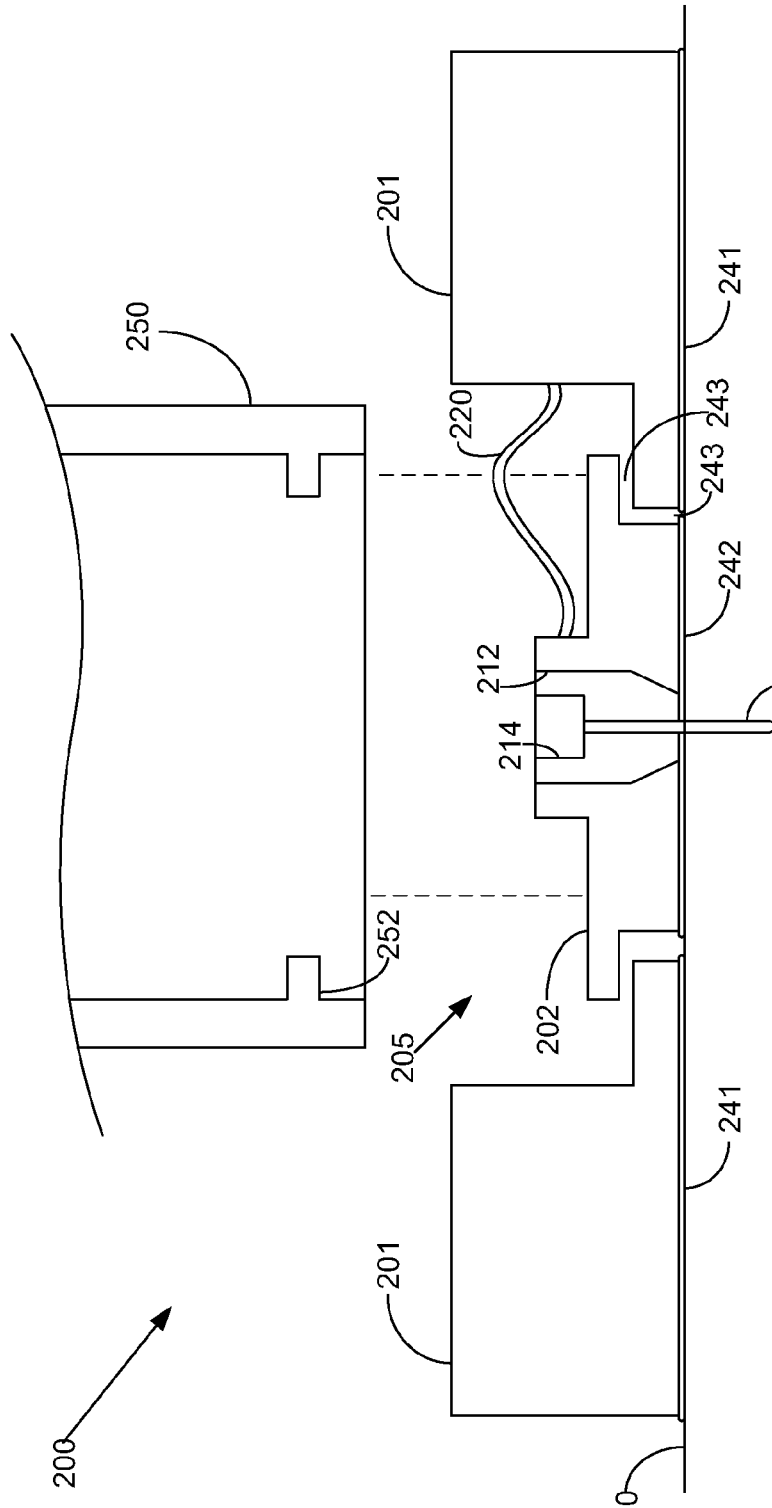

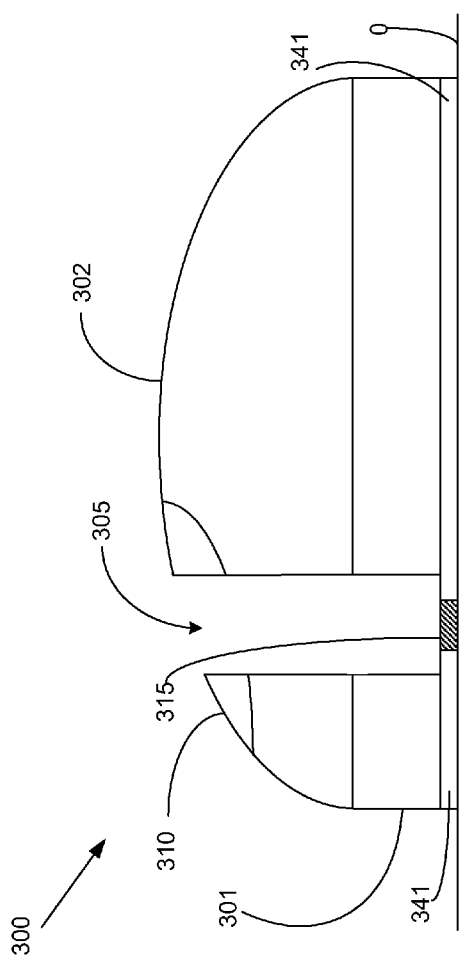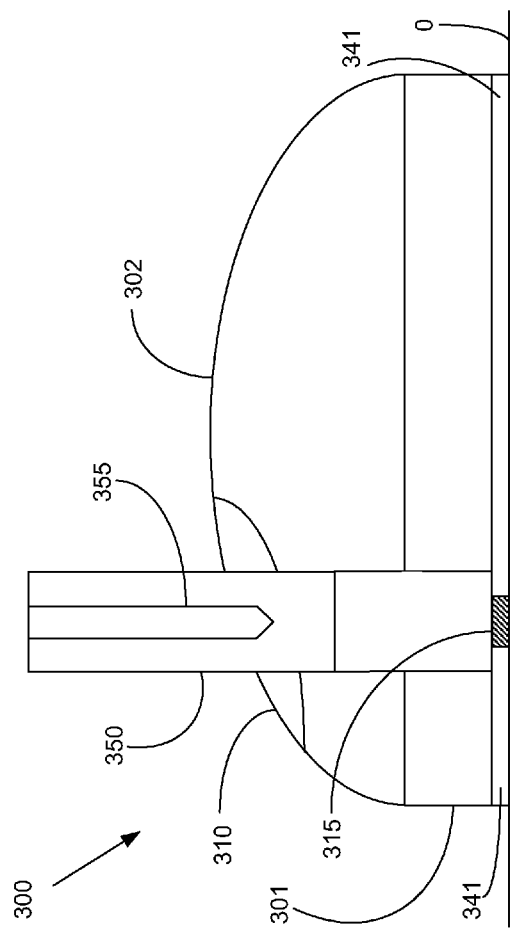

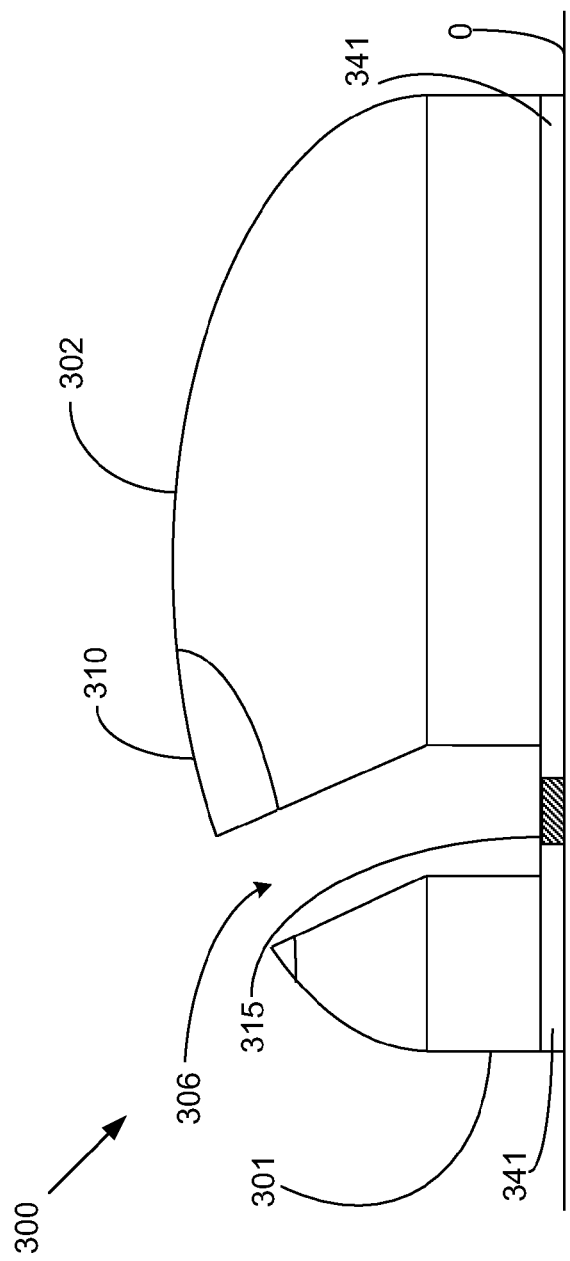

NEEDLE INSERTION SYSTEMS AND METHODS

BACKGROUND OF THE INVENTION

Certain chronic diseases may be treated, according to modern medical techniques, by delivering a medication or other substance to a user-patient's body, either in a continuous manner or at particular times or time intervals within an overall time period. For example, diabetes is a chronic disease that is commonly treated by delivering defined amounts of insulin to the user-patient at appropriate times. Some common modes of providing an insulin therapy to a user-patient include delivery of insulin through manually operated syringes and insulin pens. Other modern systems employ programmable pumps to deliver controlled amounts of insulin to a user-patient.

Pump type delivery devices have been configured in external devices (that connect to a user-patient) or implantable devices (to be implanted inside of a user-patient's body). External pump type delivery devices include devices designed for use in a generally stationary location (for example, in a hospital or clinic), and further devices configured for ambulatory or portable use (to be carried by a user-patient). Examples of some external pump type delivery devices are described in U.S. patent application Ser. No. 11/211,095, filed Aug. 23, 2005, titled "Infusion Device And Method With Disposable Portion" and Published PCT Application WO 01/70307 (PCT/US01/09139) titled "Exchangeable Electronic Cards For Infusion Devices" (each of which is owned by the assignee of the present invention), Published PCT Application WO 04/030716 (PCT/US2003/028769) titled "Components And Methods For Patient Infusion Device," Published PCT Application WO 04/030717 (PCT/US2003/029019) titled "Dispenser Components And Methods For Infusion Device," U.S. Patent Application Publication No. 2005/0065760 titled "Method For Advising Patients Concerning Doses Of Insulin," and U.S. Pat. No. 6,589,229 titled "Wearable Self-Contained Drug Infusion Device," each of which is incorporated herein by reference in its entirety.

External pump type delivery devices may be connected in fluid-flow communication to a user-patient, for example, through a suitable hollow tubing. The hollow tubing may be connected to a hollow needle that is designed to pierce the user-patient's skin and deliver an infusion medium to the user-patient. Alternatively, the hollow tubing may be connected directly to the user-patient as or through a cannula or set of micro-needles.

In contexts in which the hollow tubing is connected to the user-patient through a hollow needle that pierces the user-patient's skin, a manual insertion of the needle into the user-patient can be somewhat traumatic to the user-patient. Accordingly, insertion mechanisms have been made to assist the insertion of a needle into the user-patient, whereby a needle is forced by a spring to quickly move from a retracted position into an extended position. As the needle is moved into the extended position, the needle is quickly forced through the user-patient's skin in a single, relatively abrupt motion that can be less traumatic to certain user-patients as compared to a slower, manual insertion of a needle. While a quick thrust of the needle into the user-patient's skin may be less traumatic to some patients than a manual insertion, it is believed that, in some contexts, some patients may feel less trauma if the needle is moved a very slow, steady pace. Examples of insertion mechanisms that may be used with and may be built into a delivery device are described in: U.S. patent application Ser. No. 11/645,435, filed Dec. 26, 2006, titled "Infusion Medium Delivery system, Device And Method With Needle Inserter And Needle Inserter Device And Method,"; and U.S. patent application Ser. No. 11/211,095, filed Aug. 23, 2005, titled "Infusion Device And Method With Disposable Portion" (each of which is assigned to the assignee of the present invention), each of which is incorporated herein by reference in its entirety. Other examples of insertion tools are described in U.S. Patent Application Publication No. 2002/0022855, titled "Insertion Device For An Insertion Set And Method Of Using The Same" (assigned to the assignee of the present invention), which is incorporated herein by reference in its entirety. Other examples of needle/cannula insertion tools that may be used (or modified for use) to insert a needle and/or cannula, are described in, for example U.S. patent application Ser. No. 10/389,132 filed Mar. 14, 2003, and entitled "Auto Insertion Device For Silhouette Or Similar Products," and/or U.S. patent application Ser. No. 10/314,653 filed Dec. 9, 2002, and entitled "Insertion Device For Insertion Set and Method of Using the Same," both of which are incorporated herein by reference in their entirety.

As compared to syringes and insulin pens, pump type delivery devices can be significantly more convenient to a user-patient, in that accurate doses of insulin may be calculated and delivered automatically to a user-patient at any time during the day or night. Furthermore, when used in conjunction with glucose sensors or monitors, insulin pumps may be automatically controlled to provide appropriate doses of infusion medium at appropriate times of need, based on sensed or monitored levels of blood glucose.

Pump type delivery devices have become an important aspect of modern medical treatments of various types of medical conditions, such as diabetes. As pump technologies improve and as doctors and user-patients become more familiar with such devices, the popularity of external medical infusion pump treatment increases and is expected to increase substantially over the next decade.

SUMMARY OF THE DISCLOSURE

Various embodiments of the present invention are directed to needle-inserting devices and medical devices systems and methods. A needle-inserting device in accordance with an embodiment of the present invention may include, but is not limited to, a housing, a plunger, a bias mechanism, and a needle. The housing may have an internal chamber and a longitudinal dimension. The plunger may be arranged for movement within the internal chamber, in the direction of the longitudinal dimension of the housing, from a first plunger position to a second plunger position. The bias mechanism may be for imparting a bias force on the plunger when the plunger is in the first plunger position. The bias force may be directed toward the second plunger position. The needle may be connected to the plunger for movement with the plunger.

The plunger may have a tab end configured to retain the plunger in the first plunger position. The tab end may be moveable relative to the housing. Upon movement of the tab end, the plunger may be free to move from the first plunger position to the second plunger position under the bias force imparted by the bias mechanism to move the needle to an insert position.

In various embodiments, the tab end may be removable from the plunger. Upon removal of the tab end from the plunger, the plunger may be free to move from the first plunger position to the second plunger position under the bias force imparted by the bias mechanism to move the needle to an insert position.

In various embodiments, the tab end may be located at least partially outside the internal chamber of the housing. In other embodiments, the tab end may be configured to be broken off the plunger head. In some embodiments, the tab end may be configured to be disconnected from the plunger head. In other embodiments, the tab end may be configured to be twisted off the plunger head.

In various embodiments, the housing may have an opening that opens to the internal chamber, the opening having a width dimension. The tab end may have a width dimension larger than the width dimension of the opening. In some embodiments, the tab end may be configured to be one of rotatable and twistable to fit within the opening of the housing. In other embodiments, the tab end may be configured to be compressible to fit within the opening of the housing.

In various embodiments, at least a portion of the needle may pierce skin of a user as the plunger moves from the first plunger position to the second plunger position to move the needle to the insert position.

In various embodiments, the device may further include a hollow cannula having a hollow interior and arranged with the needle extending through the hollow interior. Upon movement of the tab end, the plunger may be free to move from the first plunger position to the second plunger position under the bias force imparted by the bias mechanism to move the hollow cannula to a cannula insert position. In some embodiments, at least a portion of the cannula may pierce skin of a user as the plunger moves from the first plunger position to the second plunger position to move the cannula to the insert position.

In various embodiments, the device may further include an insert structure arranged for movement within the internal chamber of the housing with movement of the plunger from the first plunger position to the second plunger position. The insert structure may include a body through which the needle extends. The housing may have at least one slot or groove. The body of the insert structure may include a shaped portion configured to engage the at least one slot or groove upon the insert structure being moved as the plunger moves from the first plunger position to the second plunger position.

In some embodiments, the housing may have a flexible portion near or in the vicinity of the at least one slot or groove. The body of the insert structure may be arranged to engage and outwardly flex the flexible portion of the housing upon the insert structure being moved as the plunger moves from the first plunger position to the second plunger position.

In various embodiments, the device may further include an insert structure may be arranged for movement within the internal chamber of the housing with movement of the plunger from the first plunger position to the second plunger position. The insert structure may include a body through which the needle extends. The insert structure may have a fluid channel. The fluid channel may be connectable to a reservoir when the insert structure moves with the plunger from the first plunger position to the second plunger position.

In further embodiments, the device may include a hollow cannula having a hollow interior and arranged with the needle extending through the hollow interior. Upon movement of the tab end, the plunger may be free to move from the first plunger position to the second plunger position under the bias force imparted by the bias mechanism to move the hollow cannula to an insert position. The fluid channel may be in fluid communication with the hollow interior of the cannula upon the insert structure being moved with the plunger from the first plunger position to the second plunger position.

A method of making a needle-inserting device in accordance with an embodiment of the present invention may include, but is not limited to any one or combination of, (i) providing a housing having an internal chamber and a longitudinal dimension; (ii) arranging a plunger for movement within the internal chamber, in the direction of the longitudinal dimension of the housing, from a first plunger position to a second plunger position; (iii) providing a bias mechanism for imparting a bias force on the plunger when the plunger is in the first plunger position, wherein the bias force is directed toward the second plunger position; (iv) locating a needle connected to the plunger, for movement with the plunger; and (v) configuring a tab end of the plunger to retain the plunger in the first plunger position, the tab end moveable relative to the housing such that upon movement of the tab end, the plunger is free to move from the first plunger position to the second plunger position under the bias force imparted by the bias mechanism to move the needle to an insert position.

A medical device in accordance with an embodiment of the present invention may include, but is not limited to, a medical monitoring or treatment device, a base, a structure, and a cannula. The medical monitoring or treatment device may be configured to provide a monitoring or treatment operation on a user. The base may be adapted to be secured to the user during operation of the medical monitoring or treatment device. The structure may be adapted to be secured to the user during operation of the medical monitoring or treatment device. The structure may be connected to and supported by the base. The structure may have a body. The structure and the base may be configured for relative movement there between. The cannula may extend through the body of the structure during operation of the medical monitoring or treatment device. The cannula may be for inserting into the user during operation of the medical monitoring or treatment device.

In various embodiments, the structure may be arranged to be separate and apart from the base. In various embodiments, the structure may be operatively connected to the base.

In various embodiments, the device may further include a flexible connection that may be for connecting the base and the structure. In some embodiments, at least one of the base, the structure, and the cannula may be placeable by an insertion device. The flexible connection may be adapted to release the insertion device after placement of the at least one of the base, the structure, and the cannula. In some embodiments, the flexible connection may comprise a living hinge connecting the base and the structure.

In various embodiments, the device may further include a bias member provided between the base and the structure. In various embodiments, the device may further include a fluid connection in fluid communication with the cannula and a reservoir containing fluidic media. In some In various embodiments, the device may further include a housing. The base and the structure may be adapted to fit within the housing.

In various embodiments, the base may have an interior chamber. The cannula may be supported within the interior chamber of the base. In various embodiments, the base may have an interior chamber. The structure may be supported within the interior chamber of the base.

In various embodiments, the base may have a base surface facing skin of the user during operation of the medical monitoring or treatment device. The base may have an opening through the base surface. The structure may be supported at least partially within the opening.

In some embodiments, the structure may have an inserting surface facing skin of the user during operation of the medical monitoring or treatment device. An adhesive material may be provided on at least a portion of the base surface and at least a portion of the inserting surface for securing the at least one of the base and the structure to the user. The adhesive material may have a different adhesion strength on the structure than on the base.

In various embodiments, the device may further include an adhesive material provided on at least a portion of the structure and at least a portion of the base for securing the at least one of the base and the structure to the user. The adhesive material may have a different adhesion strength on the structure than on the base.

In various embodiments, the device may further include an adhesive material provided on at least a first portion of the structure and at least a second portion of the structure for securing the structure to the user. The adhesive material may have a different adhesion strength on the first portion than on the second portion.

In various embodiments, the device may further include an adhesive material provided on at least a first portion of the base and at least a second portion of the base for securing the base to the user. The adhesive material may have a different adhesion strength on the first portion than on the second portion.

In various embodiments, at least one of the base, the structure, and the cannula may be placeable by an insertion device. In various embodiments, the structure may comprise a sensor for sensing a parameter of the user during operation of the medical monitoring or treatment device.

In various embodiments, the device may include a sensor that may be for sensing a parameter of the user during operation of the medical monitoring or treatment device. The sensor may be operatively connected to and supported by the structure.

A method of making a medical device in accordance with an embodiment of the present invention may include, but is not limited to any one or combination of, (i) providing a medical monitoring or treatment device configured to provide a monitoring or treatment operation on a user; (ii) providing a base adapted to be secured to the user during operation of the medical monitoring or treatment device; (iii) providing a structure adapted to be secured to the user during operation of the medical monitoring or treatment device, the structure connected to and supported by the base, the structure having a body, the structure and the base configured for relative movement there between; and (iv) providing a cannula extending through the body of the structure during operation of the medical monitoring or treatment device, the cannula for inserting into the user during operation of the medical monitoring or treatment device.

A medical device in accordance with an embodiment of the present invention may include, but is not limited to, a medical monitoring or treatment device, a housing, and a magnifying material. The medical monitoring or treatment device may be configured to provide a monitoring or treatment operation on a user. The medical monitoring or treatment device may be operable with an insertion needle. The housing may be adapted to be secured to the user for supporting the medical monitoring or treatment device during operation of the medical monitoring or treatment device. The magnifying material may be arranged on the housing for increasing visibility of an injection site on skin of the user when piercing the skin of the user with the insertion needle.

In various embodiments, the housing may have an opening for inserting at least a portion of the insertion needle. The opening may be in vertical alignment with the injection site.

In various embodiments, the housing may have an opening for inserting at least a portion of the insertion needle. The opening may be disaligned with the injection site.

In various embodiments, at least a portion of the magnifying area may be located above the injection site. In various embodiments, the magnifying area may be laterally offset to the injection site.

A method of making a medical device in accordance with an embodiment of the present invention may include, but is not limited to any one or combination of, (i) providing a medical monitoring or treatment device configured to provide a monitoring or treatment operation on a user, the medical monitoring or treatment device operable with an insertion needle; (ii) providing a housing adapted to be secured to the user for supporting the medical monitoring or treatment device during operation of the medical monitoring or treatment device; and (iii) arranging a magnifying material on the housing for increasing visibility of an injection site on skin of the user when piercing the skin of the user with the insertion needle.

BRIEF DESCRIPTION OF THE DRAWINGS

FIG. 18B illustrates a cross-section of a medical device in accordance with an embodiment of the present invention;

FIG. 19A illustrates a cross-section of a medical device in accordance with an embodiment of the present invention;

FIG. 19B illustrates a cross-section of a medical device in accordance with an embodiment of the present invention; and FIG. 20 illustrates a cross-section of a medical device in accordance with an embodiment of the present invention.

DETAILED DESCRIPTION OF THE PREFERRED EMBODIMENTS

Figure 1:
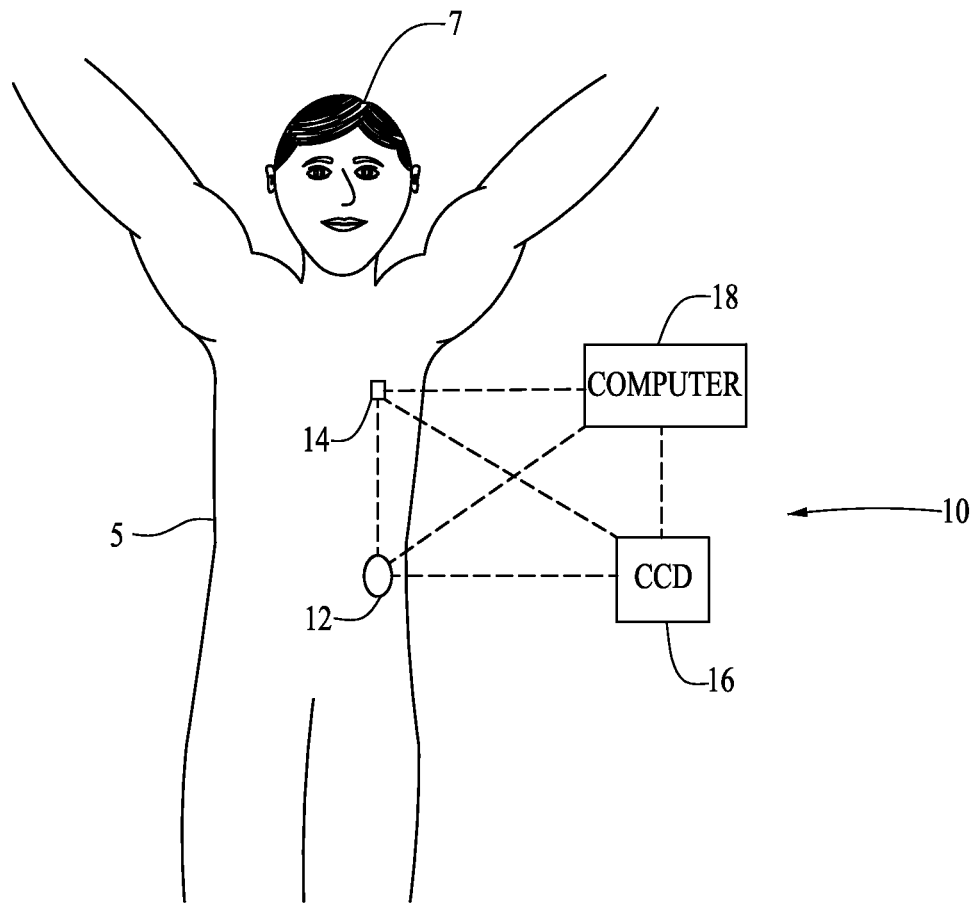
FIG. 1 illustrates a generalized representation of a system in accordance with an embodiment of the present invention.

FIG. 1 illustrates a generalized representation of a system 10 in accordance with an embodiment of the present invention. The system 10 includes a delivery device 12. The system 10 may further include a sensing device 14, a command control device (CCD) 16, and a computer 18. In various embodiments, the delivery device 12 and the sensing device 14 may be secured at desired locations on the body 5 of a patient or user-patient 7. The locations at which the delivery device 12 and the sensing device 14 are secured to the body 5 of the user-patient 7 in FIG. 1 are provided only as representative, non-limiting, examples.

The system 10, delivery device 12, sensing device 14, CCD 16 and computer 18 may be similar to those described in the following U.S. patent applications that were assigned to the assignee of the present invention, however, with a reservoir and plunger configuration such as described herein with reference to FIGS. 7-8C, where each of following patent applications is incorporated herein by reference in its entirety: (i) U.S. patent application Ser. No. 11/211,095, filed Aug. 23, 2005, "Infusion Device And Method With Disposable Portion"; (ii) U.S. patent application Ser. No. 11/515,225, filed Sep. 1, 2006, "Infusion Medium Delivery Device And Method With Drive Device For Driving Plunger In Reservoir"; (iii) U.S. patent application Ser. No. 11/588,875, filed Oct. 27, 2006, "Systems And Methods Allowing For Reservoir Filling And Infusion Medium Delivery"; (iv) U.S. patent application Ser. No. 11/588,832, filed Oct. 27, 2006, "Infusion Medium Delivery Device And Method With Drive Device For Driving Plunger In Reservoir"; (v) U.S. patent application Ser. No. 11/588,847, filed Oct. 27, 2006, "Infusion Medium Delivery Device And Method With Compressible Or Curved Reservoir Or Conduit"; (vi) U.S. patent application Ser. No. 11/589,323, filed Oct. 27, 2006, "Infusion Pumps And Methods And Delivery Devices And Methods With Same"; (vii) U.S. patent application Ser. No. 11/602,173, filed Nov. 20, 2006, "Systems And Methods Allowing For Reservoir Filling And Infusion Medium Delivery"; (viii) U.S. patent application Ser. No. 11/602,052, filed Nov. 20, 2006, "Systems And Methods Allowing For Reservoir Filling And Infusion Medium Delivery"; (ix) U.S. patent application Ser. No. 11/602,428, filed Nov. 20, 2006, "Systems And Methods Allowing For Reservoir Filling And Infusion Medium Delivery"; (x) U.S. patent application Ser. No. 11/602,113, filed Nov. 20, 2006, "Systems And Methods Allowing For Reservoir Filling And Infusion Medium Delivery"; (xi) U.S. patent application Ser. No. 11/604,171, filed Nov. 22, 2006, "Infusion Medium Delivery Device And Method With Drive Device For Driving Plunger In Reservoir"; (xii) U.S. patent application Ser. No. 11/604,172, filed Nov. 22, 2006, "Infusion Medium Delivery Device And Method With Drive Device For Driving Plunger In Reservoir"; (xiii) U.S. patent application Ser. No. 11/606,703, filed Nov. 30, 2006, "Infusion Pumps And Methods And Delivery Devices And Methods With Same"; (xiv) U.S. patent application Ser. No. 11/606,836, filed Nov. 30, 2006, "Infusion Pumps And Methods And Delivery Devices And Methods With Same"; U.S. patent application Ser. No. 11/636,384, filed Dec. 8, 2006, "Infusion Medium Delivery Device And Method With Compressible Or Curved Reservoir Or Conduit"; (xv) U.S. patent application Ser. No. 11/645,993, filed Dec. 26, 2006, "Infusion Medium Delivery Device And Method With Compressible Or Curved Reservoir Or Conduit"; U.S. patent application Ser. No. 11/645,972, filed Dec. 26, 2006, "Infusion Medium Delivery System, Device And Method With Needle Inserter And Needle Inserter Device And Method"; (xvi) U.S. patent application Ser. No. 11/646,052, filed Dec. 26, 2006, "Infusion Medium Delivery System, Device And Method With Needle Inserter And Needle Inserter Device And Method"; (xvii) U.S. patent application Ser. No. 11/645,435, filed Dec. 26, 2006, "Infusion Medium Delivery System, Device And Method With Needle Inserter And Needle Inserter Device And Method"; (xviii) U.S. patent application Ser. No. 11/646,000, filed Dec. 26, 2006, "Infusion Medium Delivery System, Device And Method With Needle Inserter And Needle Inserter Device And Method"; and (xix) U.S. patent application Ser. No. 11/759,725, filed Jun. 7, 2007, "Infusion Medium Delivery Device And Method With Drive Device For Driving Plunger In Reservoir". In other embodiments, the system 10, delivery device 12, sensing device 14, CCD 16, and computer 18 may have other suitable configurations.

The delivery device 12 is configured to deliver fluidic media to the body 5 of the user-patient 7. In various embodiments, fluidic media includes a liquid, a fluid, a gel, or the like. In some embodiments, fluidic media includes a medicine or a drug for treating a disease or a medical condition. For example, fluidic media may include insulin for treating diabetes, or may include a drug for treating pain, cancer, a pulmonary disorder, HIV, or the like. In some embodiments, fluidic media includes a nutritional supplement, a dye, a tracing medium, a saline medium, a hydration medium, or the like.

The sensing device 14 includes a sensor, a monitor, or the like, for providing sensor data or monitor data. In various embodiments, the sensing device 14 may be configured to sense a condition of the user-patient 7. For example, the sensing device 14 may include electronics and enzymes reactive to a biological condition, such as a blood glucose level, or the like, of the user-patient 7. In various embodiments, the sensing device 14 may be secured to the body 5 of the user-patient 7 or embedded in the body 5 of the user-patient 7 at a location that is remote from the location at which the delivery device 12 is secured to the body 5 of the user-patient 7. In various other embodiments, the sensing device 14 may be incorporated within the delivery device 12.

In further embodiments, the sensing device 14 and/or the delivery device 12 may utilize a closed-loop system. Examples of sensing devices and/or delivery devices utilizing closed-loop systems may be found at, but are not limited to, the following references: (i) U.S. Pat. No. 6,088,608, entitled "Electrochemical Sensor And Integrity Tests Therefor"; (ii) U.S. Pat. No. 6,119,028, entitled "Implantable Enzyme-Based Monitoring Systems Having Improved Longevity Due To Improved Exterior Surfaces"; (iii) U.S. Pat. No. 6,589,229, entitled "Implantable Enzyme-Based Monitoring Systems Adapted for Long Term Use"; (iv) U.S. Pat. No. 6,740,072, entitled "System And Method For Providing Closed Loop Infusion Formulation Delivery"; (v) U.S. Pat. No. 6,827,702, entitled "Safety Limits For Closed-Loop Infusion Pump Control"; (vi) U.S. Pat. No. 7,323,142, entitled "Sensor Substrate And Method Of Fabricating Same"; (vii) U.S. patent application Ser. No. 09/360,342, filed Jul. 22, 1999, entitled "Substrate Sensor"; and (viii) U.S. Provisional Patent Application Ser. No. 60/318,060, filed Sep. 7, 2001, entitled "Sensing Apparatus and Process", all of which are incorporated herein by reference in their entirety.

In such embodiments, the sensing device 14 may be configured to sense a condition of the user-patient 7, such as, but not limited to, blood glucose level, or the like. The delivery device 12 may be configured to deliver fluidic media in response to the condition sensed by the sensing device 14. In turn, the sensing device 14 may continue to sense a new condition of the user-patient, allowing the delivery device 12 to deliver fluidic media continuously in response to the new condition sensed by the sensing device 14 indefinitely. In other embodiments, the sensing device 14 and/or the delivery device 12 may be configured to utilize the closed-loop system only for a portion of the day, for example only when the user-patient is asleep or awake.

Each of the delivery device 12, the sensing device 14, the CCD 16, and the computer 18 may include transmitter, receiver, or transceiver electronics that allow for communication with other components of the system 10. The sensing device 14 may be configured to transmit sensor data or monitor data to the delivery device 12. The sensing device 14 may also be configured to communicate with the CCD 16. The delivery device 12 may include electronics and software that are configured to analyze sensor data and to deliver fluidic media to the body 5 of the user-patient 7 based on the sensor data and/or preprogrammed delivery routines.

The CCD 16 and the computer 18 may include electronics and other components configured to perform processing, delivery routine storage, and to control the delivery device 12. By including control functions in the CCD 16 and/or the computer 18, the delivery device 12 may be made with more simplified electronics. However, in some embodiments, the delivery device 12 may include all control functions, and may operate without the CCD 16 and the computer 18. In various embodiments, the CCD 16 may be a portable electronic device. In addition, in various embodiments, the delivery device 12 and/or the sensing device 14 may be configured to transmit data to the CCD 16 and/or the computer 18 for display or processing of the data by the CCD 16 and/or the computer 18.

Examples of the types of communications and/or control capabilities, as well as device feature sets and/or program options may be found in the following references: (i) U.S. patent application Ser. No. 10/445,477, filed May 27, 2003, entitled "External Infusion Device with Remote Programming, Bolus Estimator and/or Vibration Alarm Capabilities"; (ii) U.S. patent application Ser. No. 10/429,385, filed May 5, 2003, entitled "Handheld Personal Data Assistant (PDA) with a Medical Device and Method of Using the Same"; and (iii) U.S. patent application Ser. No. 09/813,660, filed Mar. 21, 2001, entitled "Control Tabs for Infusion Devices and Methods of Using the Same", all of which are incorporated herein by reference in their entirety.

Figure 2:
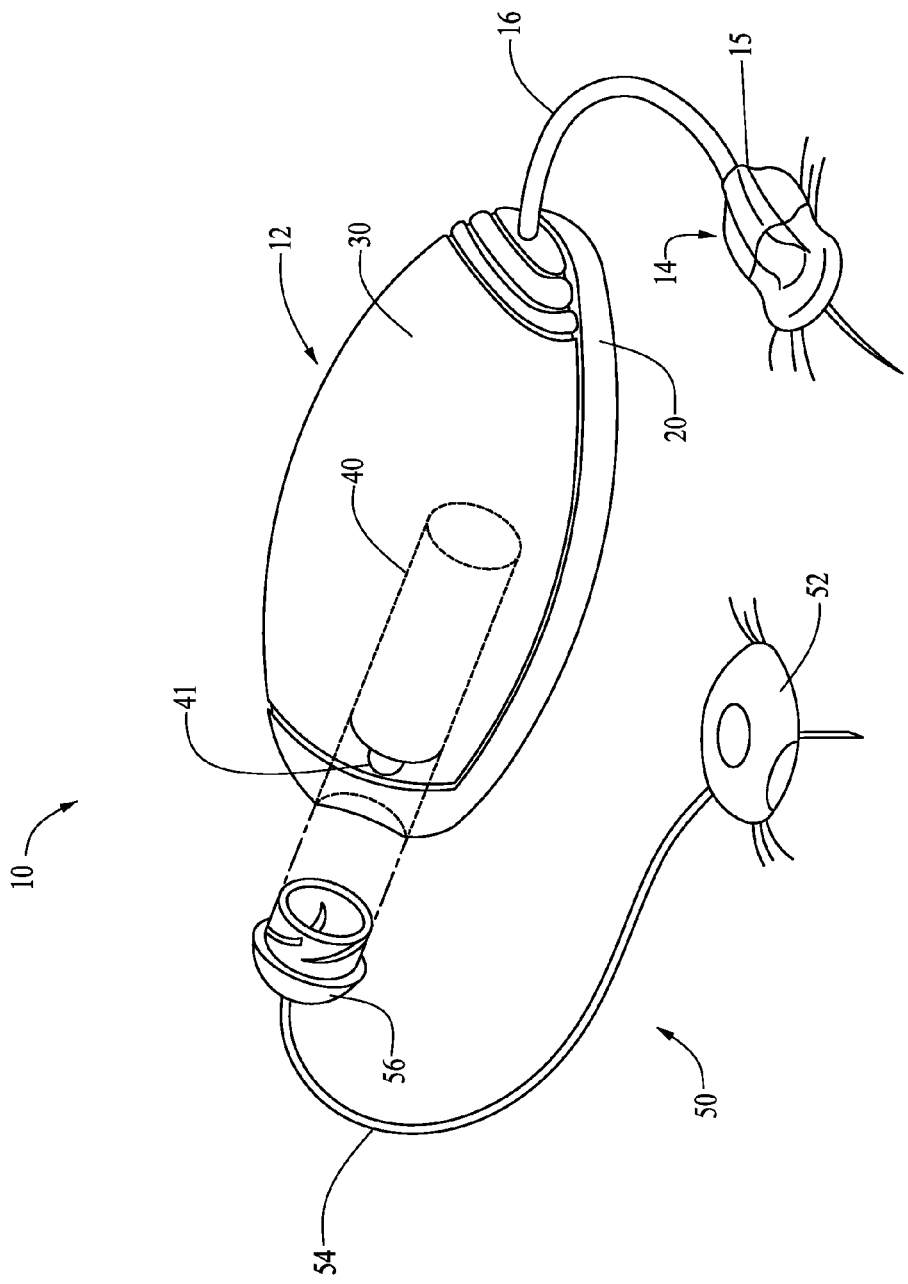
FIG. 2 illustrates an example of a system in accordance with an embodiment of the present invention.

FIG. 2 illustrates an example of the system 10 in accordance with an embodiment of the present invention. The system 10 in accordance with the embodiment illustrated in FIG. 2 includes the delivery device 12 and the sensing device 14. The delivery device 12 in accordance with an embodiment of the present invention includes a disposable housing 20, a durable housing 30, and a reservoir system 40. The delivery device 12 may further include an infusion path 50.

Elements of the delivery device 12 that ordinarily contact the body of a user-patient or that ordinarily contact fluidic media during operation of the delivery device 12 may be considered as a disposable portion of the delivery device 12. For example, a disposable portion of the delivery device 12 may include the disposable housing 20 and the reservoir system 40. The disposable portion of the delivery device 12 may be recommended for disposal after a specified number of uses.

On the other hand, elements of the delivery device 12 that do not ordinarily contact the body of the user-patient or fluidic media during operation of the delivery device 12 may be considered as a durable portion of the delivery device 12. For example, a durable portion of the delivery device 12 may include the durable housing 30, electronics (not shown in FIG. 2), a drive device having a motor and drive linkage (not shown in FIG. 2), and the like. Elements of the durable housing portion of the delivery device 12 are typically not contaminated from contact with the user-patient or fluidic media during normal operation of the delivery device 12 and, thus, may be retained for re-use with replaced disposable portions of the delivery device 12.

In various embodiments, the disposable housing 20 supports the reservoir system 40 and has a bottom surface (facing downward and into the page in FIG. 2) that is configured to secure to the body of a user-patient. An adhesive may be employed at an interface between the bottom surface of the disposable housing 20 and the skin of a user-patient, so as to adhere the disposable housing 20 to the skin of the user-patient. In various embodiments, the adhesive may be provided on the bottom surface of the disposable housing 20, with a peelable cover layer covering the adhesive material. In this manner, the cover layer may be peeled off to expose the adhesive material, and the adhesive side of the disposable housing 20 may be placed against the user-patient, for example against the skin of the user-patient. Thus in some embodiments, the delivery device 12 may be attached to the skin of the user-patient.

In other embodiments, the disposable housing 20 and/or the remaining portions of the delivery device 12 may be worn or otherwise attached on or underneath clothing of the user-patient. Similarly, the delivery device 12 may be supported by any suitable manner, such as, but not limited to, on a belt, in a pocket, and the like. Representative examples of such delivery devices 12 may include, but is not limited to, the MiniMed Paradigm 522 Insulin Pump, MiniMed Paradigm 722 Insulin Pump, MiniMed Paradigm 515 Insulin Pump, MiniMed Paradigm 715 Insulin Pump, MiniMed Paradigm 512R Insulin Pump, MiniMed Paradigm 712R Insulin Pump, MiniMed 508 Insulin Pump, MiniMed 508R Insulin Pump, and any other derivatives thereof.

The reservoir system 40 is configured for containing or holding fluidic media, such as, but not limited to insulin. In various embodiments, the reservoir system 40 includes a hollow interior volume for receiving fluidic media, such as, but not limited to, a cylinder-shaped volume, a tubular-shaped volume, or the like. In some embodiments, the reservoir system 40 may be provided as a cartridge or canister for containing fluidic media. In various embodiments, the reservoir system 40 is able to be refilled with fluidic media. In further embodiments, the reservoir system 40 is pre-filled with fluidic media.

The reservoir system 40 may be supported by the disposable housing 20 in any suitable manner. For example, the disposable housing 20 may be provided with projections or struts (not shown), or a trough feature (not shown), for holding the reservoir system 40. In some embodiments, the reservoir system 40 may be supported by the disposable housing 20 in a manner that allows the reservoir system 40 to be removed from the disposable housing 20 and replaced with another reservoir. Alternatively, or in addition, the reservoir system 40 may be secured to the disposable housing 20 by a suitable adhesive, a strap, or other coupling structure.

In various embodiments, the reservoir system 40 includes a port 41 for allowing fluidic media to flow into and/or flow out of the interior volume of the reservoir system 40. In some embodiments, the infusion path 50 includes a connector 56, a tube 54, and a needle apparatus 52. The connector 56 of the infusion path 50 may be connectable to the port 41 of the reservoir system 40. In various embodiments, the disposable housing 20 is configured with an opening near the port 41 of the reservoir system 40 for allowing the connector 56 of the infusion path 50 to be selectively connected to and disconnected from the port 41 of the reservoir system 40.

In various embodiments, the port 41 of the reservoir system 40 is covered with or supports a septum (not shown in FIG. 2), such as a self-sealing septum, or the like. The septum may be configured to prevent fluidic media from flowing out of the reservoir system 40 through the port 41 when the septum is not pierced. The septum (not shown) may be for inhibiting contamination of the port 41 of the reservoir 40 when the connector 56 of the infusion path 50 is disconnected from the port 41 of the reservoir 40. Also, in various embodiments, the connector 56 of the infusion path 50 may include a needle for piercing the septum (not shown) covering the port 41 of the reservoir system 40 so as to allow fluidic media to flow out of the interior volume of the reservoir system 40.

Examples of needle/septum connectors can be found in U.S. patent application Ser. No. 10/328,393, filed Dec. 22, 2003, entitled "Reservoir Connector," which is incorporated herein by reference in its entirety. In other alternatives, non-septum connectors such as Luer locks, or the like may be used. In various embodiments, the needle apparatus 52 of the infusion path 50 includes a needle that is able to puncture the skin of a user-patient. In addition, in various embodiments, the tube 54 connects the connector 56 with the needle apparatus 52 and is hollow, such that the infusion path 50 is able to provide a path to allow for the delivery of fluidic media from the reservoir system 40 to the body of a user-patient.

The durable housing 30 of the delivery device 12 in accordance with various embodiments of the present invention includes a housing shell configured to mate with and secure to the disposable housing 20. The durable housing 30 and the disposable housing 20 may be provided with correspondingly shaped grooves, notches, tabs, or other suitable features, that allow the two parts to easily connect together, by manually pressing the two housings together, by twist or threaded connection, or other suitable manner of connecting the parts that is well known in the mechanical arts.

In various embodiments, the durable housing 30 and the disposable housing 20 may be connected to each other using a twist action. The durable housing 30 and the disposable housing 20 may be configured to be separable from each other when a sufficient force is applied to disconnect the two housings from each other. For example, in some embodiments the disposable housing 20 and the durable housing 30 may be snapped together by friction fitting. In various embodiments, a suitable seal, such as an o-ring seal, may be placed along a peripheral edge of the durable housing 30 and/or the disposable housing 20, so as to provide a seal against water entering between the durable housing 30 and the disposable housing 20.

The durable housing 30 of the delivery device 12 may support a drive device (not shown in FIG. 2), including a motor and a drive device linkage portion, for applying a force to fluidic media within the reservoir system 40 to force fluidic media out of the reservoir system 40 and into an infusion path, such as the infusion path 50, for delivery to a user-patient. For example, in some embodiments, an electrically driven motor may be mounted within the durable housing 30 with appropriate linkage for operatively coupling the motor to a plunger arm (not shown in FIG. 2) connected to a plunger head (not shown in FIG. 2) that is within the reservoir system 40 and to drive the plunger head in a direction to force fluidic media out of the port 41 of the reservoir system 40 and to the user-patient.

Also, in some embodiments, the motor may be controllable to reverse direction so as to move the plunger arm and the plunger head to cause fluid to be drawn into the reservoir system 40 from a patient. The motor may be arranged within the durable housing 30 and the reservoir system 40 may be correspondingly arranged on the disposable housing 20, such that the operable engagement of the motor with the plunger head, through the appropriate linkage, occurs automatically upon the user-patient connecting the durable housing 30 with the disposable housing 20 of the delivery device 12. Further examples of linkage and control structures may be found in U.S. patent application Ser. No. 09/813,660, filed Mar. 21, 2001, entitled "Control Tabs for Infusion Devices and Methods of Using the Same", which is incorporated herein by reference in its entirety.

In various embodiments, the durable housing 30 and the disposable housing 20 may be made of suitably rigid materials that maintain their shape, yet provide sufficient flexibility and resilience to effectively connect together and disconnect, as described above. The material of the disposable housing 20 may be selected for suitable compatibility with skin. For example, the disposable housing 20 and the durable housing 30 of the delivery device 12 may be made of any suitable plastic, metal, composite material, or the like. The disposable housing 20 may be made of the same type of material or a different material relative to the durable housing 30. In some embodiments, the disposable housing 20 and the durable housing 30 may be manufactured by injection molding or other molding processes, machining processes, or combinations thereof.

For example, the disposable housing 20 may be made of a relatively flexible material, such as a flexible silicone, plastic, rubber, synthetic rubber, or the like. By forming the disposable housing 20 of a material capable of flexing with the skin of a user-patient, a greater level of user-patient comfort may be achieved when the disposable housing 20 is secured to the skin of the user-patient. In addition, a flexible disposable housing 20 may result in an increase in site options on the body of the user-patient at which the disposable housing 20 may be secured. In some embodiments, the disposable housing 20 may include an adhesive material, as described below, for attaching the disposable housing 20 to the user-patient or other portions of the medical device, such as, but not limited to, the durable housing 30.

In the embodiment illustrated in FIG. 2, the delivery device 12 is connected to the sensing device 14 through a connection element 16 of the sensing device 14. The sensing device 14 may include a sensor 15 that includes any suitable biological or environmental sensing device, depending upon a nature of a treatment to be administered by the delivery device 12. For example, in the context of delivering insulin to a diabetes patient, the sensor 15 may include a blood glucose sensor, or the like.

In some embodiments, the sensor 15 may include a continuous glucose sensor. The continuous glucose sensor may be implantable within the body of the user-patient. In other embodiments, the continuous glucose sensor may be located externally, for example on the skin of the user-patient, or attached to clothing of the user-patient. In such embodiments, fluid may be drawn continually from the user-patient and sensed by the continuous glucose sensor. In various embodiments, the continuous glucose sensor may be configured to sense and/or communicate with the CCD 16 continuously. In other embodiments, the continuous glucose sensor may be configured to sense and/or communicate with the CCD 16 intermittently, for example sense glucose levels and transmit information every few minutes. In various embodiments, the continuous glucose sensor may utilize glucose oxidase.

The sensor 15 may be an external sensor that secures to the skin of a user-patient or, in other embodiments, may be an implantable sensor that is located in an implant site within the body of the user-patient. In further alternatives, the sensor may be included with as a part or along side the infusion cannula and/or needle, such as for example as shown in U.S. patent application Ser. No. 11/149,119, filed Jun. 8, 2005, entitled "Dual Insertion Set", which is incorporated herein by reference in its entirety. In some embodiments, the sensor 15 may be integrated with the disposable housing 20. In the illustrated example of FIG. 2, the sensor 15 is an external sensor having a disposable needle pad that includes a needle for piercing the skin of the user-patient and enzymes and/or electronics reactive to a biological condition, such as blood glucose level or the like, of the user-patient. In this manner, the delivery device 12 may be provided with sensor data from the sensor 15 secured to the user-patient at a site remote from the location at which the delivery device 12 is secured to the user-patient.

While the embodiment shown in FIG. 2 includes a sensor 15 connected by the connection element 16 for providing sensor data to sensor electronics (not shown in FIG. 2) located within the durable housing 30 of the delivery device 12, other embodiments may employ a sensor 15 located within the delivery device 12. Yet other embodiments may employ a sensor 15 having a transmitter for communicating sensor data by a wireless communication link with receiver electronics (not shown in FIG. 2) located within the durable housing 30 of the delivery device 12. In various embodiments, a wireless connection between the sensor 15 and the receiver electronics within the durable housing 30 of the delivery device 12 may include a radio frequency (RF) connection, an optical connection, or another suitable wireless communication link. Further embodiments need not employ the sensing device 14 and, instead, may provide fluidic media delivery functions without the use of sensor data.

As described above, by separating disposable elements of the delivery device 12 from durable elements, the disposable elements may be arranged on the disposable housing 20, while durable elements may be arranged within a separable durable housing 30. In this regard, after a prescribed number of uses of the delivery device 12, the disposable housing 20 may be separated from the durable housing 30, so that the disposable housing 20 may be disposed of in a proper manner. The durable housing 30 may then be mated with a new (unused) disposable housing 20 for further delivery operation with a user-patient.

Figure 3:
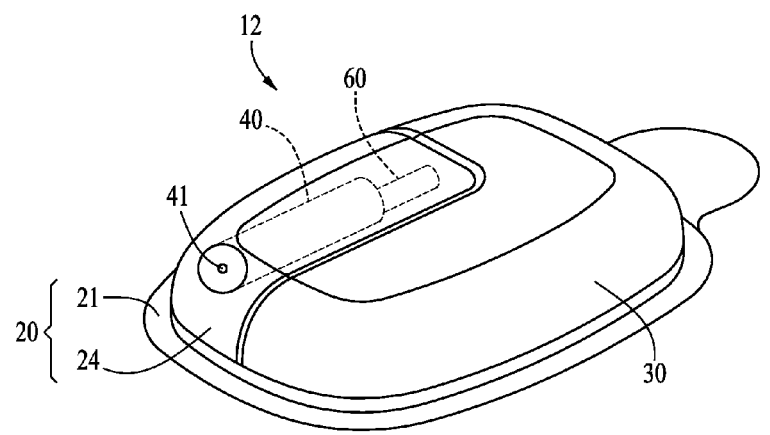
FIG. 3 illustrates an example of a delivery device in accordance with an embodiment of the present invention.

FIG. 3 illustrates an example of the delivery device 12 in accordance with another embodiment of the present invention. The delivery device 12 of the embodiment of FIG. 3 is similar to the delivery device 12 of the embodiment of FIG. 2. While the delivery device 12 in the embodiment illustrated in FIG. 2 provides for the durable housing 30 to cover the reservoir system 40, the delivery device 12 in the embodiment of FIG. 3 provides for the durable housing 30 to secure to the disposable housing 20 without covering the reservoir system 40. The delivery device 12 of the embodiment illustrated in FIG. 3 includes the disposable housing 20, and the disposable housing 20 in accordance with the embodiment illustrated in FIG. 3 includes a base 21 and a reservoir retaining portion 24. In one embodiment, the base 21 and reservoir retaining portion 24 may be formed as a single, unitary structure.

The base 21 of the disposable housing 20 is configured to be secured to the body of a user-patient. The reservoir-retaining portion 24 of the disposable housing 20 is configured to house the reservoir system 40. The reservoir-retaining portion 24 of the disposable housing 20 may be configured to have an opening to allow for the port 41 of the reservoir system 40 to be accessed from outside of the reservoir-retaining portion 24 while the reservoir system 40 is housed in the reservoir-retaining portion 24. The durable housing 30 may be configured to be attachable to and detachable from the base 21 of the disposable housing 20. The delivery device 12 in the embodiment illustrated in FIG. 3 includes a plunger arm 60 that is connected to or that is connectable to a plunger head (not shown in FIG. 3) within the reservoir system 40.

Figure 4:
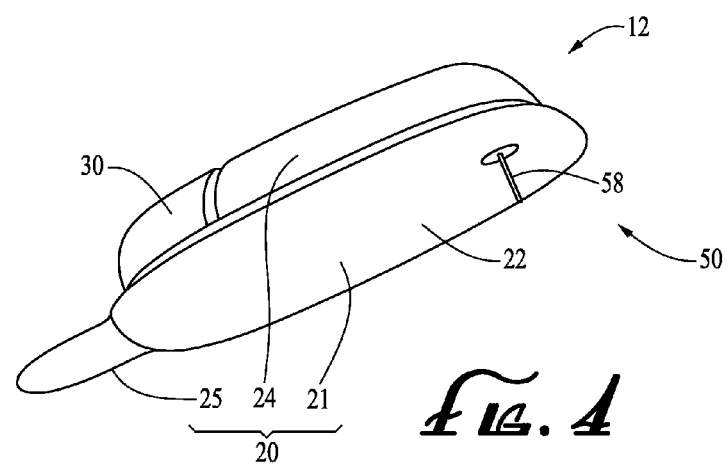
FIG. 4 illustrates a delivery device in accordance with an embodiment of the present invention.

FIG. 4 illustrates another view of the delivery device 12 of the embodiment of FIG. 3. The delivery device 12 of the embodiment illustrated in FIG. 4 includes the disposable housing 20, the durable housing 30, and the infusion path 50. The disposable housing 20 in the embodiment of FIG. 4 includes the base 21, the reservoir-retaining portion 24, and a peelable cover layer 25. The peelable cover layer 25 may cover an adhesive material on the bottom surface 22 of the base 21. The peelable cover layer 25 may be configured to be peelable by a user-patient to expose the adhesive material on the bottom surface 22 of the base 21. In some embodiments, there may be multiple adhesive layers on the bottom surface 22 of the base 21 that are separated by peelable layers.

The infusion path 50 in accordance with the embodiment of the present invention illustrated in FIG. 4 includes the needle 58 rather than the connector 56, the tube 54, and the needle apparatus 52 as shown in the embodiment of FIG. 2. The base 21 of the disposable housing 20 may be provided with an opening or pierceable wall in alignment with a tip of the needle 58, to allow the needle 58 to pass through the base 21 and into the skin of a user-patient under the base 21, when extended. In this manner, the needle 58 may be used to pierce the skin of the user-patient and deliver fluidic media to the user-patient.

Alternatively, the needle 58 may be extended through a hollow cannula (not shown in FIG. 4), such that upon piercing the skin of the user-patient with the needle 58, an end of the hollow cannula is guided through the skin of the user-patient by the needle 58. Thereafter, the needle 58 may be removed, leaving the hollow cannula in place, with one end of the cannula located within the body of the user-patient and the other end of the cannula in fluid flow connection with fluidic media within the reservoir system 40, to convey pumped infusion media from the reservoir system 40 to the body of the user-patient.

Figure 5A:
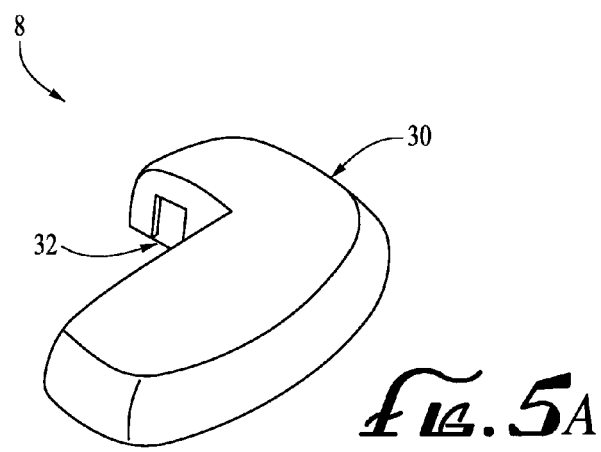
FIG. 5A illustrates a durable portion of a delivery device in accordance with an embodiment of the present invention.
Figure 5B:
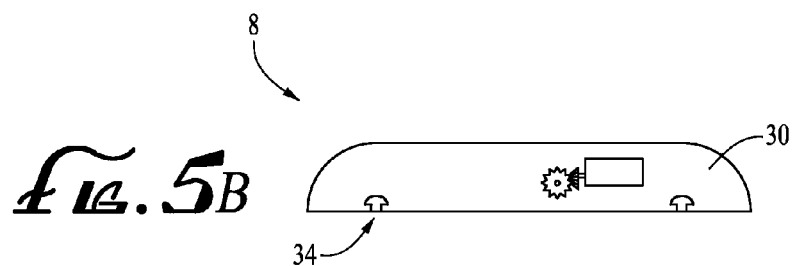
FIG. 5B illustrates a section view of a durable portion of a delivery device in accordance with an embodiment of the present invention.
Figure 5C:
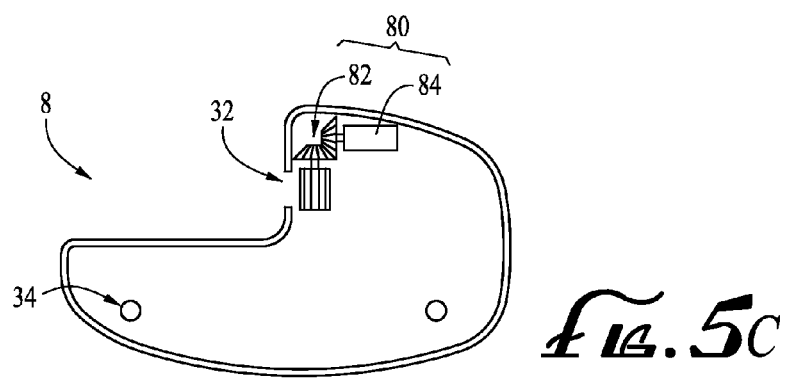
FIG. 5C illustrates a section view of a durable portion of a delivery device in accordance with an embodiment of the present invention.

FIG. 5A illustrates a durable portion 8 of the delivery device 12 (refer to FIG. 3) in accordance with an embodiment of the present invention. FIG. 5B illustrates a section view of the durable portion 8 in accordance with an embodiment of the present invention. FIG. 5C illustrates another section view of the durable portion 8 in accordance with an embodiment of the present invention. With reference to FIGS. 5A, 5B, and 5C, in various embodiments, the durable portion 8 includes the durable housing 30, and a drive device 80. The drive device 80 includes a motor 84 and a drive device linkage portion 82.

In various embodiments, the durable housing 30 may include an interior volume for housing the motor 84, the drive device linkage portion 82, other electronic circuitry, and a power source (not shown in FIGS. 5A, 5B, and 5C). In addition, in various embodiments, the durable housing 30 is configured with an opening 32 for receiving a plunger arm 60 (refer to FIG. 3). In addition, in various embodiments, the durable housing 30 may include one or more connection members 34, such as tabs, insertion holes, or the like, for connecting with the base 21 of the disposable housing 20 (refer to FIG. 3).

Figure 6A:
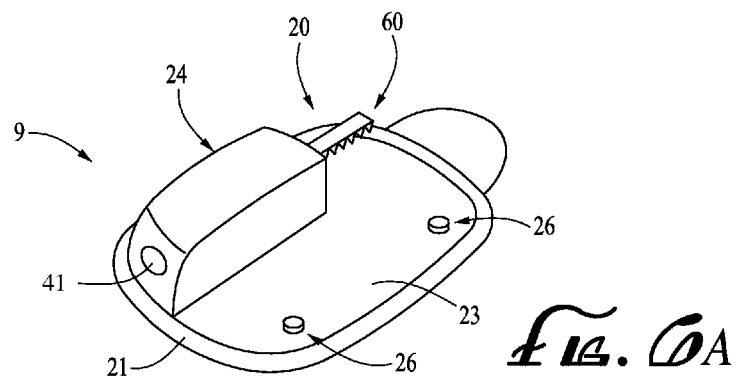
FIG. 6A illustrates a disposable portion of a delivery device in accordance with an embodiment of the present invention.
Figure 6B:
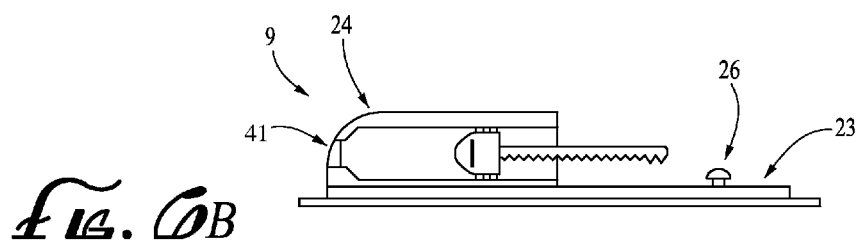
FIG. 6B illustrates a section view of a disposable portion of a delivery device in accordance with an embodiment of the present invention.
Figure 6C:
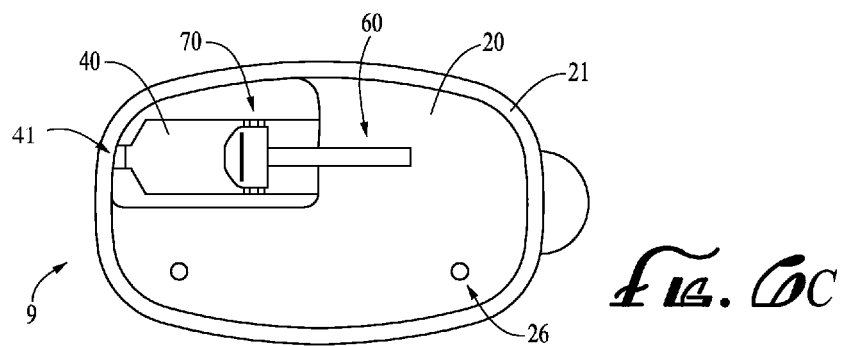
FIG. 6C illustrates a section view of a disposable portion of a delivery device in accordance with an embodiment of the present invention.

FIG. 6A illustrates a disposable portion 9 of the delivery device 12 (refer to FIG. 3) in accordance with an embodiment of the present invention. FIG. 6B illustrates a section view of the disposable portion 9 in accordance with an embodiment of the present invention. FIG. 6C illustrates another section view of the disposable portion 9 in accordance with an embodiment of the present invention. With reference to FIGS. 6A, 6B, and 6C, in various embodiments, the disposable portion 9 includes the disposable housing 20, the reservoir system 40, the plunger arm 60, and a plunger head 70. In some embodiments, the disposable housing 20 includes the base 21 and the reservoir-retaining portion 24. In various embodiments, the base 21 includes a top surface 23 having one or more connection members 26, such as tabs, grooves, or the like, for allowing connections with the one or more connection members 34 of embodiments of the durable housing 30 (refer to FIG. 5B).

In various embodiments, the reservoir system 40 is housed within the reservoir retaining portion 24 of the disposable housing 20, and the reservoir system 40 is configured to hold fluidic media. In addition, in various embodiments, the plunger head 70 is disposed at least partially within the reservoir system 40 and is moveable within the reservoir system 40 to allow fluidic media to fill into the reservoir system 40 and to force fluidic media out of the reservoir system 40. In some embodiments, the plunger arm 60 is connected to or is connectable to the plunger head 70.

Also, in some embodiments, a portion of the plunger arm 60 extends to outside of the reservoir-retaining portion 24 of the disposable housing 20. In various embodiments, the plunger arm 60 has a mating portion for mating with the drive device linkage portion 82 of the drive device 80 (refer to FIG. 5C). With reference to FIGS. 5C and 6C, in some embodiments, the durable housing 30 may be snap fitted onto the disposable housing 20, whereupon the drive device linkage portion 82 automatically engages the mating portion of the plunger arm 60.

When the durable housing 30 and the disposable housing 20 are fitted together with the drive device linkage portion 82 engaging or mating with the plunger arm 60, the motor 84 may be controlled to drive the drive device linkage portion 82 and, thus, move the plunger arm 60 to cause the plunger head 70 to move within the reservoir system 40. When the interior volume of the reservoir system 40 is filled with fluidic media and an infusion path is provided from the reservoir system 40 to the body of a user-patient, the plunger head 70 may be moved within the reservoir system 40 to force fluidic media from the reservoir system 40 and into the infusion path, so as to deliver fluidic media to the body of the user-patient.

In various embodiments, once the reservoir system 40 has been sufficiently emptied or otherwise requires replacement, a user-patient may simply remove the durable housing 30 from the disposable housing 20, and replace the disposable portion 9, including the reservoir system 40, with a new disposable portion having a new reservoir. The durable housing 30 may be connected to the new disposable housing of the new disposable portion, and the delivery device including the new disposable portion may be secured to the skin of a user-patient, or otherwise attached to the user-patient.

In various other embodiments, rather than replacing the entire disposable portion 9 every time the reservoir system 40 is emptied, the reservoir system 40 may be refilled with fluidic media. In some embodiments, the reservoir system 40 may be refilled while remaining within the reservoir retaining portion 24 (refer to FIG. 6B) of the disposable housing 20. In addition, in various embodiments, the reservoir system 40 may be replaced with a new reservoir (not shown), while the disposable housing 20 may be re-used with the new reservoir. In such embodiments, the new reservoir may be inserted into the disposable portion 9.

With reference to FIGS. 3, 5A, 6B, and 6C, in various embodiments, the delivery device 12 includes reservoir status circuitry (not shown), and the reservoir system 40 includes reservoir circuitry (not shown). In various embodiments, the reservoir circuitry stores information such as, but not limited to, at least one of (i) an identification string identifying the reservoir system 40; (ii) a manufacturer of the reservoir system 40; (iii) contents of the reservoir system 40; and (iv) an amount of contents in the reservoir system 40. In some embodiments, the delivery device 12 includes the reservoir status circuitry (not shown), and the reservoir status circuitry is configured to read data from the reservoir circuitry when the reservoir system 40 is inserted into the disposable portion 9.

In various embodiments, the reservoir status circuitry is further configured to store data to the reservoir circuitry after at least some of the contents of the reservoir system 40 have been transferred out of the reservoir system 40, so as to update information in the reservoir circuitry related to an amount of contents still remaining in the reservoir system 40. In some embodiments, the reservoir status circuitry is configured to store data to the reservoir circuitry, so as to update information in the reservoir circuitry related to an amount of contents still remaining in the reservoir system 40, when the reservoir system 40 is inserted into the disposable portion 9. In some embodiments, the delivery device 12 includes the reservoir status circuitry (not shown) and the reservoir system 40 includes the reservoir circuitry (not shown), and the reservoir status circuitry selectively inhibits use of the delivery device 12 or selectively provides a warning signal based on information read by the reservoir status circuitry from the reservoir circuitry.

Aspects of the present invention relate, generally, to needle inserter or inserting devices and methods and medical devices, such as, but not limited to sensors, monitors and infusion medium delivery systems, devices and methods that include such needle-inserting devices and methods. The needle-inserting device and method may operate to insert a needle or cannula through skin of a user-patient, for example, to provide a fluid flow path for conveying an infusion medium through a hollow channel in the needle or cannula and into the user-patient and/or to convey a fluid from the user-patient to one or more sensor elements. Embodiments of the present invention may be configured, as described herein, to provide a reliable, cost effective, and easy-to-use mechanism for inserting a needle or cannula to a specific depth into a user-patient with minimal traumatic effect.

In addition, embodiments may be configured to establish a contiguous fluid flow passage for fluid transfer between a reservoir and the user-patient when the hollow needle or cannula is inserted into the user-patient. Needle-inserting devices according to embodiments of the present invention may be used with, connectable to and disconnectable from, or incorporated in a portion of an infusion medium delivery system. For example, a needle-inserting device may be connectable to a base structure of a pump-type delivery device for insertion of a needle, after which the needle-inserting device may be removed from the base structure, whereupon a further housing portion of the delivery device (containing components such as, but not limited to, a reservoir and pump or drive device) may be coupled to the base structure for operation. Alternatively, the needle-inserting device may be incorporated into the further housing portion that contains other components as described above. In yet other embodiments, the needle-inserting device may be connectable to (and releasable from) or incorporated within an injection site module or other housing that connects, for example, by flexible tubing, to other components of a medical device (such as, but not limited to an infusion medium delivery device). In yet other embodiments, needle inserter devices may be configured for use with systems other than infusion medium delivery systems, such as, but not limited to sensor and monitor systems, or the like.

The structure and method described with respect to FIGS. 7-12 may be employed in any suitable device or system in which two members that, at some period of time, are not connected in fluid flow communication, are to be connected together in a manner that allows fluid to flow from one member to the other. In one example embodiment, the structure and method is described with respect to a first member including a fluid reservoir for containing an infusion medium that may be connectable to a second member including an injection site structure in which a hollow needle or cannula is or may be inserted into a user-patient, for conveying fluid media to the user-patient. However, a connection structure according to embodiments of the present invention may be employed to connect any two (or more) members together for fluid flow communication with each other.

In FIGS. 7-12, an example of a structure 100 and method for connecting two members in fluid flow communication is described with reference to a first member 102 and a second member 103. The first member 102 in the illustrated example includes a housing 104 on a base 106. The housing 104 may be formed integral with the base 106 or may be formed as a separate structure that is connected to the base 106 in a fixed relation to the base 106. The housing 104 and base 106 each may be made of any suitably rigid material, including, but not limited to plastic, metal, ceramic, composite material, or the like.

The housing 104 in the illustrated example includes a section 105 containing an injection site structure, in which a hollow needle or cannula may be inserted into a user-patient for conveying fluidic media to or from the user-patient. In other embodiments, instead of or in addition to an injection site, the housing 104 may contain, be part of, or be operatively connected to any other suitable structure for conveying, containing, and/or processing fluidic media.

The second member 103 may also include a housing 108, which, in the illustrated embodiment, is a housing of a reservoir for containing an infusion media. The second member 103 may be held within or otherwise be covered by a further housing member 109 configured to attach to the base 106. The further housing 109 may connect to the base 106 of the first member 102 by any suitable connection structure. In particular embodiments, at least one of the housing 109 and the base 106 may include one or more flexible pawls, protrusions, indentations, or the like for engaging and/or receiving one or more corresponding pawls, protrusions, indentations, or the like on the other of the base 106 and the housing 109, to provide a suitable connection structure. Alternatively or in addition, the connection structure may include adhesive material or other suitable connectors.

In other embodiments, the housing 108 may be (or be connected to) a sensor housing (not shown) that contains sensor components. In yet other embodiments, the housing 108 may contain, be part of, or be operatively connected to any other suitable structure for conveying, containing, and/or processing fluidic media. The housing 108 may be made of any suitably rigid material, including, but not limited to, plastic, metal, ceramic, composite material, or the like.

The housing 104 may have or (be connected to) a receptacle structure 110. The receptacle structure 110 may have an opening 112 in the housing leading into a chamber 114 within the receptacle structure 110. In the illustrated embodiment, the receptacle structure 110 is part of the housing 104, adjacent the section of the housing 104 that contains the injection site. In other embodiments, the receptacle structure 110 may include a further housing connected to the housing 104.

The receptacle structure 110 may include a first septum 116 located within the chamber 114 and may be moveable within the chamber 114 toward and away from the opening 112. The receptacle structure 110 may also include a bias mechanism 118, which may apply a bias force on the first septum 116 in a direction toward the opening 112. The bias mechanism 118 may force the first septum 116 against the opening 112, wherein one or more annular protrusions (or one or more appropriately shaped or positioned protrusions) 120 adjacent the opening 112 may be provided to inhibit the first septum 116 from being forced out of the chamber 114 through the opening 112.

The first septum 116 may have a front surface 116a that is at least partially exposed through the opening 112 when the first septum 116 is urged against the opening 112 by the bias mechanism 118. The first septum 116 may have a back surface 116b facing toward an interior of the chamber 114. The first septum 116 may be made of any suitable material that may be pierceable by the needle 124, such as, but not limited to, a natural or synthetic rubber material, silicon, or the like. In some embodiments, the first septum 116 may be made of a self-sealing material capable of sealing itself after a needle has pierced the first septum 116 and was subsequently withdrawn from the first septum 116.

In the illustrated embodiment, the bias mechanism 118 is a coil spring located within the chamber 114, on the opposite side of the first septum 116 with respect to the side of the first septum 116 facing the opening 112. In other embodiments, the bias mechanism 118 may be provided by other suitable means for biasing the first septum 116 toward the opening 112. These may include, but are not limited to, other types of springs, pressurized fluid within the chamber 114, a collapsible skirt structure 122 extending from the first septum 116 with a natural or built-in spring force, chemical, or substance that expands upon contact with another chemical or substance or upon application of energy from an energy source such as a heat, laser, or other radiation source, or the like.

A hollow needle 124 may be supported within the chamber 114. The hollow needle 124 may have a sharp end 124a directed toward the back surface 116b of the first septum 116. In the illustrated embodiment, the hollow needle 124 is supported within the coil spring bias mechanism 118, such that its longitudinal axial dimension extends generally parallel to the longitudinal axial dimension of the coil spring. The hollow needle 124 may be supported by a supporting structure 126 located within the receptacle structure. In the illustrated embodiment, the supporting structure 126 is a wall integral with the housing of the receptacle structure 110 and is located on the opposite end of the chamber 114 relative to the end of the chamber 114 at which the opening 112 is located. However, in other embodiments, the supporting structure 126 may be any suitable structure that is generally fixed relative to the housing of the receptacle structure 110 and is able to support the needle 124 in a generally fixed relation to the housing of the receptacle structure 110.

The hollow needle 124 may be made of any suitably rigid material, including, but not limited to metal, plastic, ceramic, or the like, and may have a hollow channel that extends in a lengthwise dimension of the needle 124. The hollow channel in the needle 124 may be open on the sharp end 124a of the needle 124 and may be open at another location 124b along the length of the needle 124, such as, but not limited to, the needle end that is opposite to the sharp end 124a. The hollow channel in the needle 124 may provide a fluid flow path between the sharp end 124a of the needle 124 and the opening 124b of the needle 124. In the illustrated embodiment, the opening 124b of the hollow needle 124 may be connected in fluid flow communication with a manifold 128 in a needle injector structure described below.

The housing 108 of the second member 103 may include a connection portion 130 having a hollow interior chamber 132 and an opening 134 into the interior chamber 132. A second septum 136 may be supported by the housing 108 to seal the opening 134. The second septum 136 may be supported in a fixed relation to the housing 108, for example, within the housing 108 at one end of the interior chamber 132.

The connection portion 130 of the housing 108 may have a suitable shape and size to fit at least partially within the opening 112 of the receptacle structure 110 in the first member 102 when the first and second members 102 and 103 are connected together. In the drawings of FIGS. 7 and 8, the first and second members 102 and 103 are shown in a separated, disconnected relation, wherein the connection portion 130 of the housing 108 is outside of the opening 112 of the receptacle structure 110. By moving the first and second members 102 and 103 together to insert the connection portion 130 into the opening 112 of the housing 108, an end surface 138 of the connection portion 130 may be urged against the moveable first septum 116. This may cause the moveable first septum 116 to move relative to the housing 108 against the force of the bias mechanism 118 toward the interior of the chamber 114. As the first septum 116 is moved toward the interior of the housing 108, the sharp end 124a of the needle 124 may pierce the first septum 116. Continued relative movement of the first and second members 102 and 103 together may cause the sharp end 124a of the needle 124 to pass through the first septum 116 in the first member 102 and then pierce and pass through the septum 136 in the second member 103.

When the first and second members 102 and 103 are brought together as described above and as shown in FIG. 9, at least a portion of the connection portion 130 may extend inside of the housing of the receptacle structure 110. In addition, the hollow needle 124 (refer to FIG. 8) may pierce the first and second septa 116 and 136 to form a fluid flow path between the interior chamber 132 (refer to FIG. 8) of the connection portion 130 and the manifold 128 (refer to FIG. 8) (or other structure at the opening 124b of the needle 124). The receptacle structure 110 and the connection portion 130 may be provided with mating connectors that provide, for example, a snap or friction connection upon the first and second members 102 and 103 being brought together as shown in FIG. 9. In one embodiment, the mating connectors may include a protrusion (not shown) on one or the other of the receptacle structure 110 and the connection portion 130. While the other of the receptacle structure 110 and the connection portion 130 may include a groove or indentation (not shown) arranged to engage each other in a snap-fitting manner upon the connection portion 130 being extended into the receptacle structure 110 a suitable distance.

As mentioned above, in the illustrated embodiment, shown in FIGS. 7-12, the opening 124b of the needle 124 is connected in fluid flow communication with the manifold 128 in an injection site structure. The injection site structure may be provided within the section 105 of the housing 104 and includes a channel 140 extending through the housing 104 and the base 106. The channel 140 may have an open end 140a on a bottom surface (relative to the orientation shown in FIG. 8) of the base 106. The channel 140 may have another open end 140b at an upper surface (relative to the orientation shown in FIG. 8) of the section 105 of the housing 104. The manifold 128 may be located along a length of the channel 140 and may be in fluid flow communication with the channel 140. Accordingly, the hollow needle 124 may be arranged in fluid flow communication with the interior of the channel 140 through the manifold 128. The channel 140 may include a channel section 142 having a larger radial dimension relative to the rest of the channel 140 and may have a suitable shape and size to receive a needle and/or cannula, as described below.

A needle-inserting device 144 may be located adjacent the open end 140b of the channel 140 and arranged to selectively extend a needle and/or cannula into the open end 140b of the channel 140 and at least partially through the channel 140 as described below. The needle-inserting device 144 may be configured to be integral with or otherwise fixed to the section 105 of the housing 104 of the first member 102. Alternatively, the needle-inserting device 144 may be a separate device (relative to the housing 104) and may be selectively connected to (in alignment with the channel 140 as shown in FIG. 8) and disconnected from the section 105 of the housing 104.

In embodiments in which the needle-inserting device 144 is a separate structure that connects to and disconnects from the housing section 105, a suitable connection structure may be provided on the needle-inserting device 144 and the housing section 105 to provide a manually releasable connection between those components. In such embodiments, the connection structure may include, but is not limited to, a threaded extension on one or the other of the needle-inserting device 144 and the housing section 105 and a corresponding threaded receptacle on the other of the housing section 105 and the needle-inserting device 144 for receiving the threaded extension in threaded engagement. In other embodiments, other suitable connection structures may be employed, including, but not limited to, flexible pawls or extensions on one or the other of the needle-inserting device 144 and the housing section 105 and a corresponding aperture, stop surface, or the like on the other of the other of the housing section 105 and the needle-inserting device 144.

Figure 8:
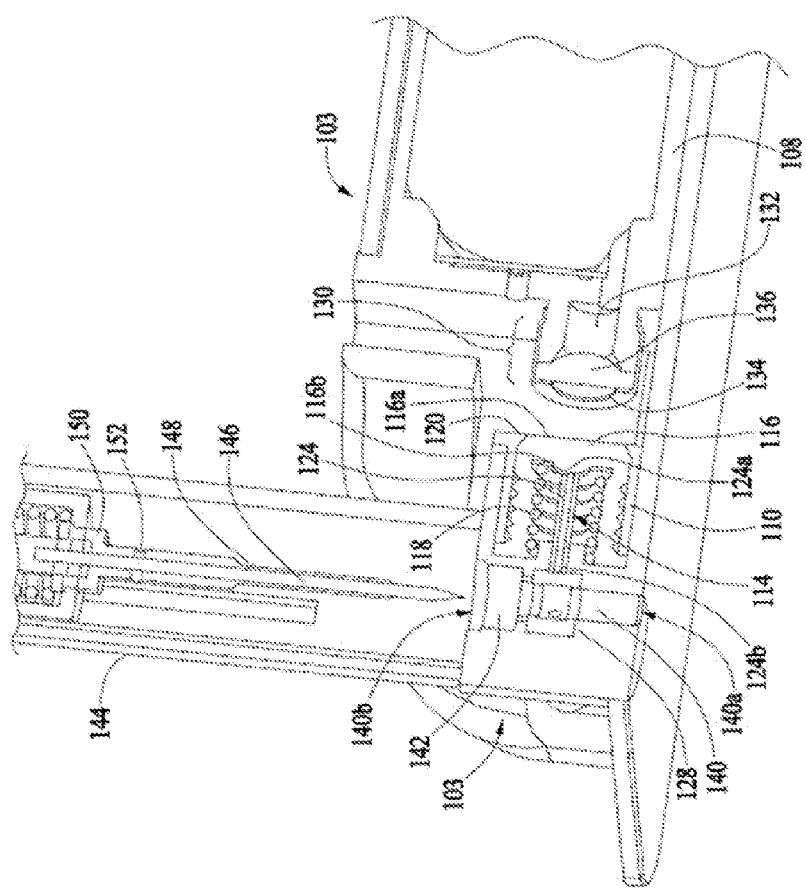
FIG. 8 illustrates a medical device in accordance with an embodiment of the present invention.
Figure 9:
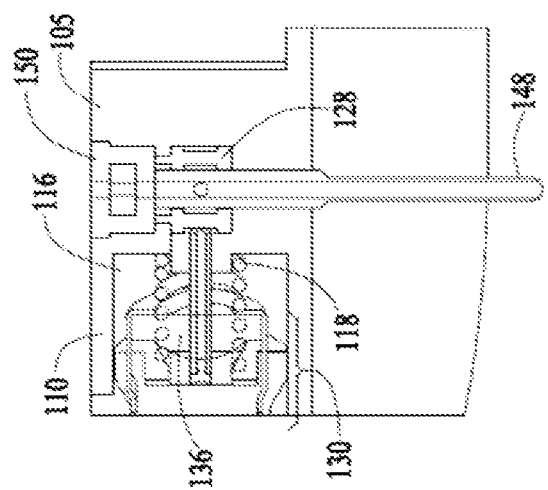
FIG. 9 illustrates a medical device in accordance with an embodiment of the present invention.
Figure 10:
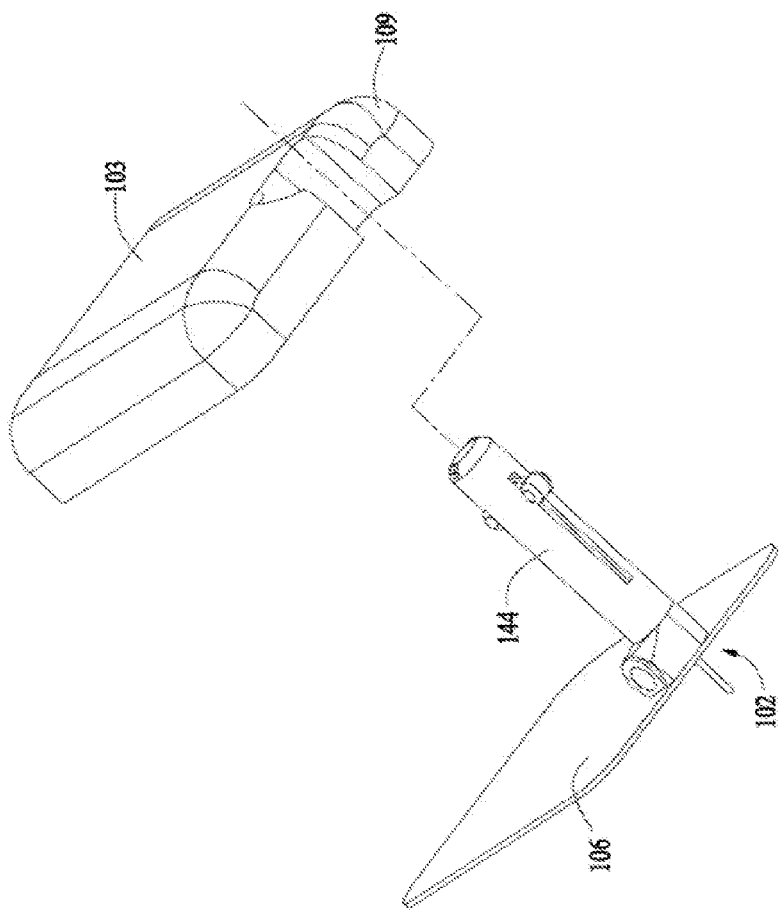
FIG. 10 illustrates a medical device in accordance with an embodiment of the present invention.
Figure 11:
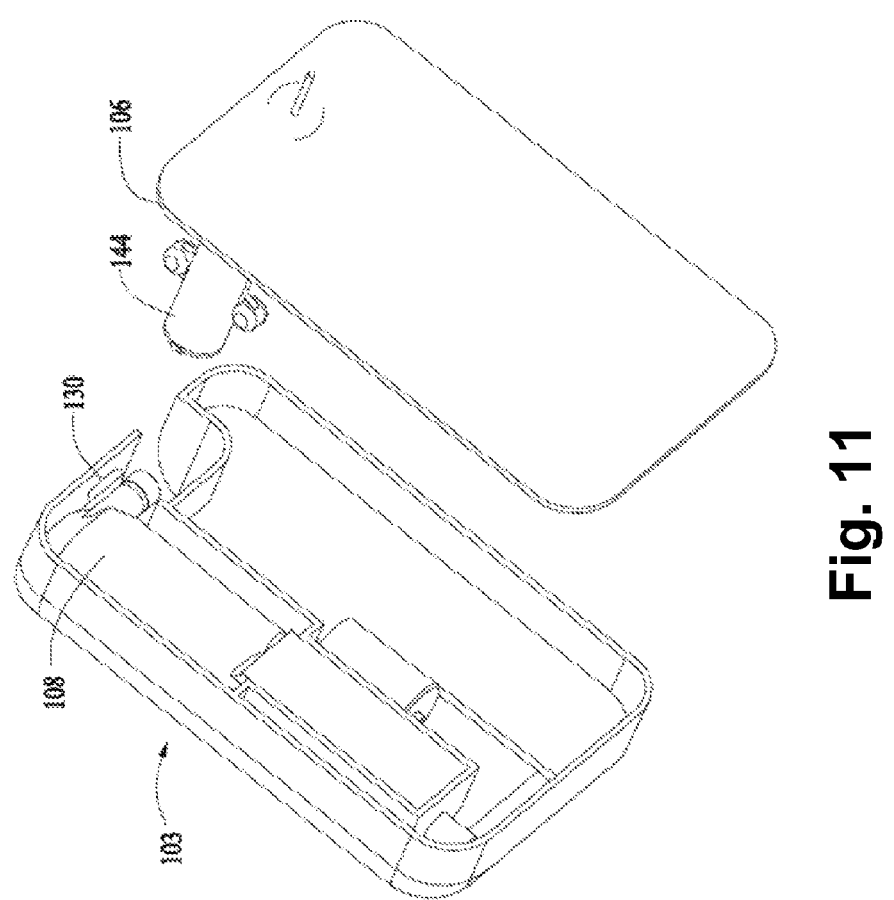
FIG. 11 illustrates a medical device in accordance with an embodiment of the present invention.
Figure 12:
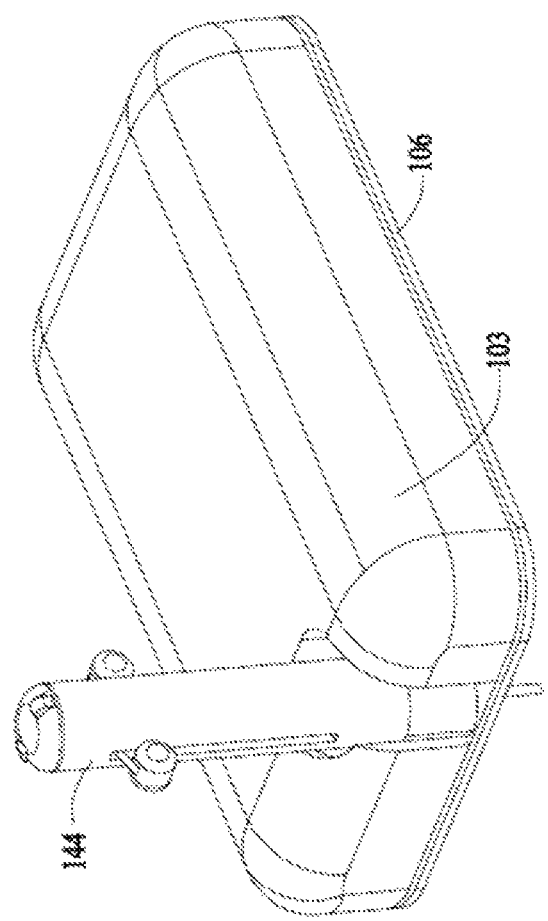
FIG. 12 illustrates a medical device in accordance with an embodiment of the present invention.

In the drawing of FIG. 8, the needle-inserting device 144 is shown as connected to the housing section 105 with a needle 146 and cannula 148 in a retracted state. The needle-inserting device 144 may be operated to selectively move the needle 146 and the cannula 148 from the retracted state (shown in FIG. 8) to an extended state (not shown) in which the needle 146 and the cannula 148 are extended through the opening 140b of the channel 140 and at least partially through the channel 140, such that the sharp end of the needle 146 and at least a portion of the length of the cannula 148 extend out the opening 140a of the channel 140. Various examples of suitable structure for needle-inserting devices are described in U.S. patent application Ser. No. 11/645,435, filed Dec. 26, 2006, entitled "Infusion Medium Delivery system, Device And Method With Needle Inserter And Needle Inserter Device And Method," which is assigned to the assignee of the present invention and is incorporated herein by reference, in its entirety. Other examples of suitable structure for needle-inserting devices are described herein.

The cannula 148 may have a hollow central channel extending along its longitudinal length and open at one end (the cannula end adjacent the sharp end of the needle 146). The other end of the cannula 148 may have a head 150 having a larger radial dimension than a shaft portion of the cannula 148. The cannula head 150 may have a suitable shape and size to fit into the section 142 of the channel 140, when the needle 146 and the cannula 148 are moved to the extended state by the needle-inserting device 144. In particular embodiments, the cannula head 150 may include one or more protrusions and/or indentations that engage with one or more corresponding indentations and/or protrusions in the channel section 142 of the housing section 105 to provide a friction fit, snap fit, or the like, to lock or retain the cannula 148 in place within the housing section 105 upon the needle 146 and cannula 148 being moved to the extended state by the needle-inserting device 144. In further embodiments, instead of or in addition to engaging protrusions and indentations, one or more other mechanical structures may be employed to provide a suitable retaining function for retaining the cannula 148 in place within the housing section 105 upon the needle 146 and the cannula 148 being moved to the extended state by the needle-inserting device 144, including, but not limited to, a friction fit structure, snap fit, or the like.

The cannula 148 may have a connection channel 152 provided in fluid flow communication with the hollow central channel of the cannula 148. The connection channel 152 may be provided, along the longitudinal length of the cannula 148, at a location at which the connection channel 152 aligns with the manifold 128 (i.e., in fluid flow communication with the interior of the manifold 128) when the needle 146 and the cannula 148 have been moved to the extended state by the needle-inserting device 144. In this manner, upon the cannula 148 being moved to the extended state, the hollow central channel of the cannula 148 may be arranged in fluid flow communication with the reservoir 108 through the manifold 128 and the connection channel 152.

Thus, according to some embodiments, in operation, a first member 102 (which may include, for example, a housing 104 that has a receptacle 110 and a injection site section 105) may be coupled together with a second member 103 (which may include, for example, a fluid reservoir housing 108) by inserting the connection portion 130 of the second member 103 into a receptacle 110 of the first member 102. Upon coupling the first and second members 102 and 103, fluid flow communication may be provided between the interior of the second member 103 and the injection site section 105 in the first member 102.

In addition, the needle-inserting device 144 may be coupled to the injection site section 105 of the housing 104 of the first member 102 (or is provided as part of a single, unitary structure with the injection site section 105 of the housing 104). The base 106 of the first member 102 may be secured to skin of a user-patient (at a suitable injection location) with, for example, but not limited to, adhesive material as described in U.S. patent application Ser. No. 11/645,435, filed Dec. 26, 2006, entitled "Infusion Medium Delivery system, Device And Method With Needle Inserter And Needle Inserter Device And Method," and/or as described herein. Alternatively or in addition, the base 106 may be secured to a user-patient by one or more other suitable structures, including, but not limited to, straps, or the like.

Once the base 106 is suitably secured to the skin of the user-patient at a suitable injection location, the inserting device 144 may be actuated to move the needle 146 and the cannula 148 from a retracted state (shown in FIG. 8) to an extended state. In the extended state, the needle 146 and the cannula 148 may pierce the skin of the user-patient adjacent the base 106. The cannula 148 may be locked into its extended state by engagement of the cannula head 150 and the channel section 142, as described above. With the cannula 148 locked in the extended state, the needle 146 may be retracted (for example, by automatic operation of the needle-inserting device 144 and/or by manual removal of the needle-inserting device 144 from the housing section 105). Once the needle 146 is removed, the cannula 148 may be held in place by the housing section 105, with a portion of the cannula 148 extending into the user-patient, and with the cannula 148 connected in fluid-flow communication with the hollow needle 124. If the first and second members 102 and 103 are connected together, as described above, then a fluid-flow connection may be provided from the reservoir 108 to the cannula 148 through the hollow needle 124 and the manifold 128.

The connection sequence (e.g., the sequence of connecting the needle-inserting device 144 to the injection site section 105 of the housing 104, connecting the receptacle 110 of the housing 104 to the connection portion 130 of the reservoir housing 108, and connecting the base 106 of the first member to the skin of the user-patient) may be different for different embodiments. In one embodiment, a user-patient may be provided with a first member 102 including the base 106 and the housing 104 (including injection site section 105) in a pre-connected state with the needle-inserting device 144. In this manner, the user-patient need not have to connect the needle-inserting device 144 to the housing 104 (as those parts are supplied to the user in a pre-connected state, for example, from a manufacturing or assembly facility). In that embodiment, the user-patient (or a medical practitioner) may secure the base 106 of the first member 102 to his or her skin, at a suitable injection location. After securing the base 106 to the skin of the user-patient, the user-patient (or a medical practitioner) may activate the needle-inserting device 144 to cause the needle 146 and the cannula 148 to be moved to the extended state and pierce the skin of the user patient.

After activation of the needle-inserting device 144, the needle-inserting device 144 may be removed from the housing section 105, leaving the cannula 148 in place within the housing section 105 and partially extended into the user-patient. With the base 106 of the first member 102 secured to the skin of the user-patient and the cannula 148 inserted at least partially into the user-patient and arranged in fluid-flow communication with the hollow needle 124, the second member 103 may be connected to the first member 102. In particular, the connection portion 130 of the housing 108 of the second member 103 may be inserted into the receptacle 110 of the housing 104 of the first member 102 to provide a fluid-flow connection between the interior of the housing 108 and the hollow needle 124 and, thus, the cannula 148. Accordingly, the interior of the housing 108, which may be a reservoir housing, for example, may be coupled in fluid-flow communication with the cannula 148 that has been extended into a user-patient for delivering fluid from the reservoir to the user-patient (or for conveying fluid from the user-patient to the reservoir).

While the connection sequence in the above embodiment involves securing the base 106 of the first member 102 to the user-patient prior to connection of the second member 103 to the first member 102, in other embodiments, the second member 103 may be connected to the first member 102 (as described above) prior to securing the base 106 of the first member onto skin of a user-patient. In such other embodiments, the first and second members 102 and 103 may be connected together and, thereafter, may be secured to a user-patient by adhering one or both of the first and second members 102 and 103 to the skin of the user-patient. Also, while the connection sequence in the above embodiment involves activating the needle-inserting device 144 prior to the connection of the second member 103 to the first member 102, in other embodiments, the second member 103 may be connected to the first member 102 (as described above) prior to activating the needle-inserting device 144.

Figure 7:
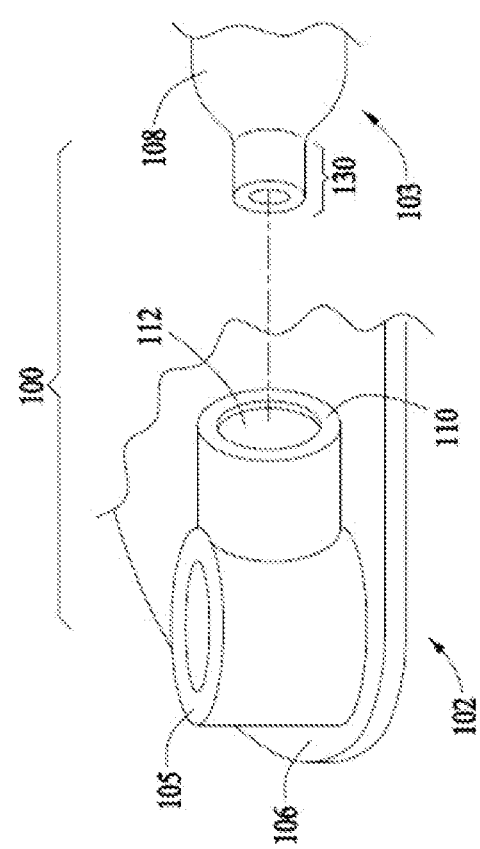
FIG. 7 illustrates portions of a medical device in accordance with an embodiment of the present invention.

In the embodiment shown in FIGS. 7 and 8, the receptacle 110 is in the first member 102 and the connection portion 130 is in the second member 103. However, in other embodiments, the receptacle 110 may be in the second member 103 (for example, in or associated with a housing for a reservoir 108) and the connection portion 130 may be in the first member 102 (for example, in or associated with a housing that contains an injection site structure). Also, in the embodiment shown in FIGS. 7 and 8, the receptacle 110 is arranged to allow the connection portion 130 of the second member 103 to be inserted in a direction substantially parallel to a plane of an upper-facing (in the orientation of FIG. 7) surface of the base 106. In the orientation of FIG. 7, this direction of insertion is shown as a horizontal direction of relative motion between the first and second members 102 and 103. However, in other embodiments, the receptacle 110 may be arranged in other suitable orientations, including, but not limited to, an orientation that allows an insertion direction (relative motion of the first and second members 102 and 103) to be substantially perpendicular to the plane of the upper-facing (in the orientation of FIG. 7) surface of the base 106. In yet other embodiments, the receptacle 110 may be arranged to allow any other suitable insertion direction at an angle transverse to the plane of the upper-facing (in the orientation of FIG. 7) surface of the base 106.

Figure 13:
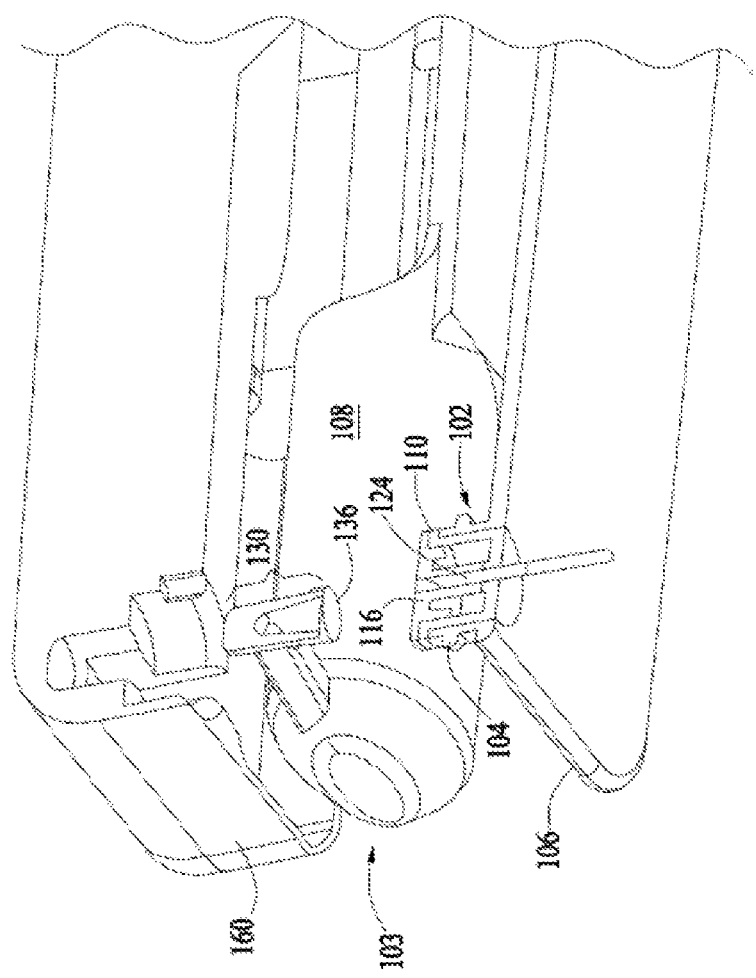
FIG. 13 illustrates a medical device in accordance with an embodiment of the present invention.
Figure 14:
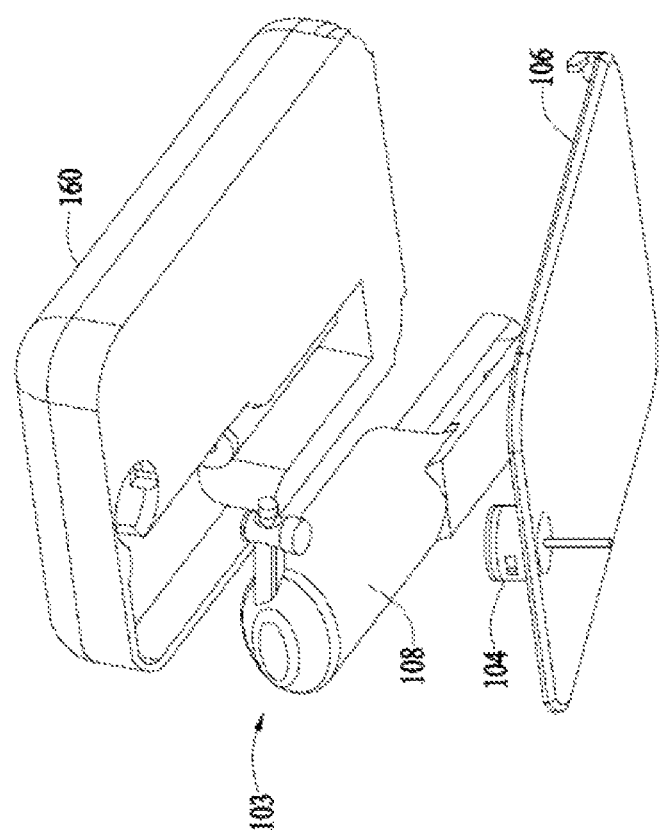
FIG. 14 illustrates a medical device in accordance with an embodiment of the present invention.

An example arrangement shown in FIGS. 13-16 provides an insertion direction (relative motion of the first and second members 102 and 103) that is substantially perpendicular to the plane of the upper-facing (in the orientation of FIG. 8) surface of the base 106. Components in FIGS. 13-16 are identified by reference numbers that are the same as reference numbers used in FIGS. 7-12 for components having similar structure and function. In FIGS. 13 and 14, the injection site structure in the housing 104 is shown in a state after a needle-inserting device has been operated to move a cannula 148 to the extended position.

Figure 15:
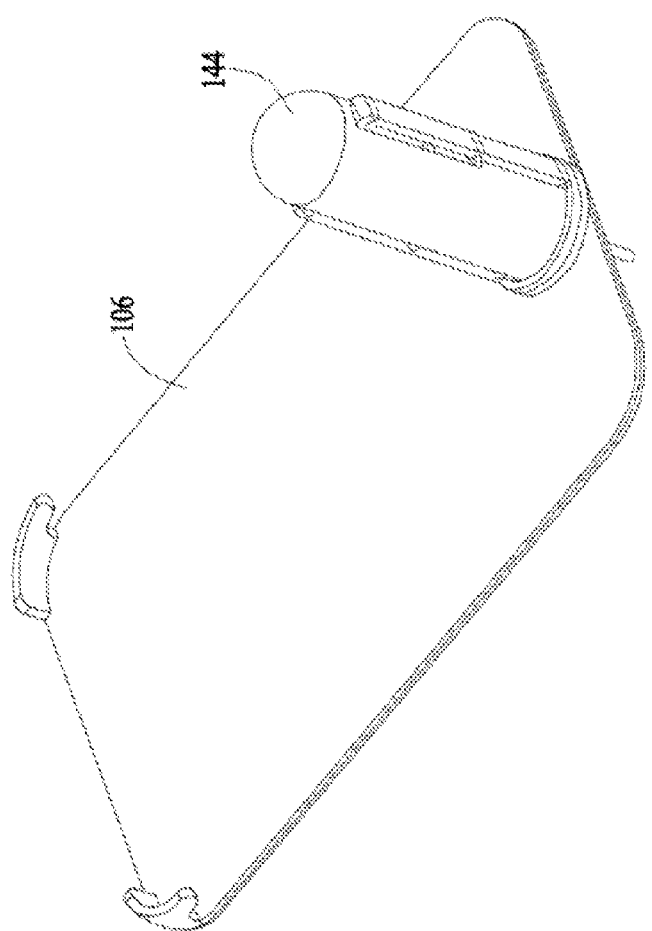
FIG. 15 illustrates a medical device in accordance with an embodiment of the present invention.
Figure 16:
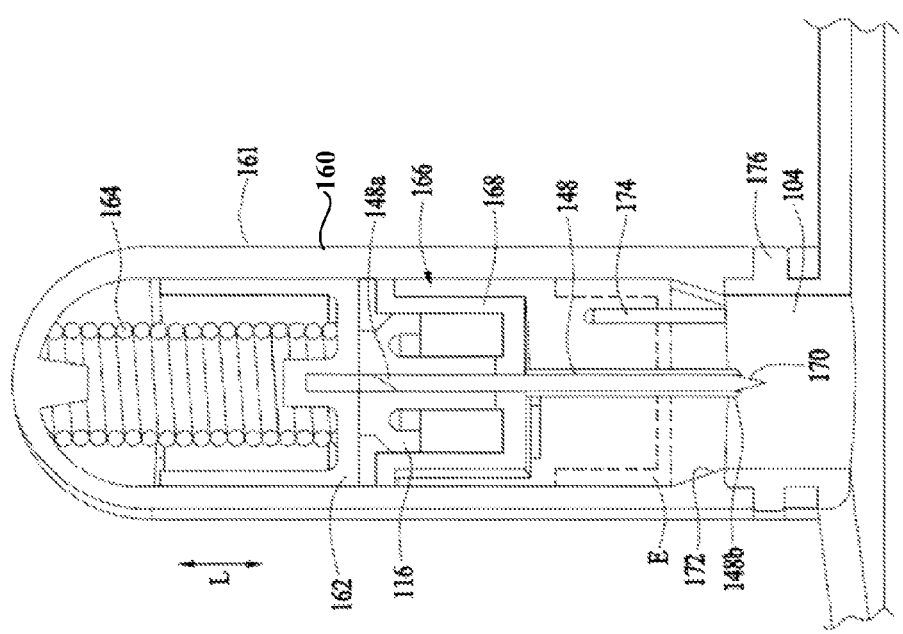
FIG. 16 illustrates cross-section of a needle-inserting device in accordance with an embodiment of the present invention.

FIGS. 15 and 16 show the base 106 of the first member 102 (of the embodiment of FIGS. 13 and 14) with a needle-inserting device 144 attached to the housing 104. The needle-inserting device 144 in FIGS. 15 and 16 includes a housing 160 that is securable to the base 106 in any suitable manner, such as, but not limited to the manners of connecting an inserting device 144 to the housing 105 discussed above with respect to the embodiment of FIGS. 7-12. As shown in FIG. 16, the housing 160 contains an internal chamber having a longitudinal dimension L and a moveable plunger 162 located within the housing 160 and moveable along the longitudinal dimension L from a retracted position (shown in solid lines in FIG. 16) to an extended position (in which the plunger 162 is moved to a position E shown in broken lines in FIG. 16).

A bias member 164, such as, but not limited to, a coil spring arranged within the housing 160 maybe configured to impart a bias force on the plunger when the plunger is in the retracted position to urge the plunger 162 toward the extended position E. A locking mechanism (not shown) may be provided such as, but not limited to, a manually moveable projection, lever, slider, or the like, that is connected to or extends through the housing 160 and engages the plunger 162 (or other structure holding the plunger 162) in a releasable manner, to selectively hold the plunger 162 in its retracted state, against the bias force of the bias member 164 and to allow a user to selectively release the plunger 162 to move in the longitudinal direction L under the force of the bias member 164.

An insert structure 166 may be arranged within the housing 160 for movement in the longitudinal direction L by action of movement of the plunger 162. The insert structure 166 may include, for example, a cup-shaped body 168. The cup-shaped body 168 may hold a first septum 116 (similar to the first septum 116 described above with respect to the embodiment of FIGS. 7-12).

A hollow cannula 148 (similar to the cannula 148 described above) may have one open end 148a that may have a sharp tip positioned adjacent the first septum 116 (or at least partially within the first septum 116). The hollow cannula 148 may extend through the cup-shaped body 168 and may have a second open end 148b. The hollow cannula 148 may be fixed to the cup-shaped member 168 to move with movement of the cup-shaped member 168. A needle 170 may be secured to the plunger 162 and may extend through the first septum 116 and cannula 148 when the plunger 162 is in the retracted position.

In operation, a user-patient (or medical practitioner) may secure the base 106 to skin of the user-patient (as described above with respect to base 106 in FIGS. 7-12). Once the base 106 is secured to the skin of the user-patient, the user-patient (or medical practitioner) may activate the needle-inserting device 144 to cause the plunger 162 to move from its retracted state to its extended state and, as a result of such movement, to cause the insert structure 166 to be moved into an opening into the interior of the housing 104. Upon movement of the insert structure 166 into the housing 104, the insert structure 166 may connect to the base housing 104 by any suitable connection structure.

As discussed above, in particular embodiments, one or the other of the cup-shaped member 168 of the insert structure 166 and the housing 104 may include one or more flexible pawls, protrusions, indentations, or the like, for engaging and receiving one or more corresponding pawls, protrusions, indentations, or the like, on the other of the housing 104 and the insert structure 166 to provide a suitable connection structure. Alternatively or in addition, the connection structure may include adhesive material or other suitable connectors.

In particular embodiments, the housing 160 of the needle-inserting device 144 may automatically release from the base 106, upon movement of the plunger 162 and the insert structure 166 from the retracted state to an extended state. For example, the housing 160 of the needle-inserting device 144 may be made of a material that has sufficient rigidity to operate as described herein, but also has a suitable flexibility (at least at the portion of the device 144 that connects to the housing 104) to bend away from and release from the housing 104, upon movement of the insert structure 166 to the extended state.

As shown in FIG. 16, a portion 172 of the internal surface of the housing 160 may include a ramped, wedge-shaped, or angled (relative to an axial direction of the housing 144, cannula 148, and needle 170) cross-sectional shape that engages an outer peripheral surface of the insert structure 166 and/or the plunger 162 as the insert structure 166 and plunger 162 are moved toward the extended state. By engaging the angled, ramped, or wedge-shaped portion 172 of the internal surface of the housing 160, the plunger 162 and/or the insert structure 166 may cause the wall(s) of the housing 160 to flex outward as the plunger 162 and/or insert structure 166 are moved into the extended position. One or more slots, grooves, or the like 174 may be formed in the housing 166 to enhance the ability of the wall(s) of the housing 160 to flex outward. One or more protrusions 176 and/or indentations may be provided on one or the other of the interior surface of the housing 166 and the exterior surface of the housing 104 for engaging one or more corresponding indentations 178 and/or protrusions in the other of the housing 104 and housing 166 when the plunger 162 and insert structure 166 are in the retracted state shown in FIG. 16.

The protrusions 176 and indentations 178, when engaged, may lock the housing 160 of the needle-inserting device 144 to the housing 104. The one or more protrusions and/or indentations may disengage from each other when the wall(s) of the housing 160 are flexed outward by the movement of the plunger 162 and the insert structure 166 to the extended state. As a result, the housing 160 of the needle-inserting device 144 may be automatically disengaged and released from the housing 104 upon movement of the plunger 162 and insert structure 166 to the extended state.

After movement of the plunger 162 and insert structure 166 from the retracted state (shown in FIG. 16) to the extended state (at which the insert structure 166 may be locked into the housing 104, while the housing 160 of the needle-inserting device 144 is released from the housing 104), the bias member 164 (or a second bias member, not shown) may act on the needle 170 to move the needle 170 toward the retracted position and, thus, withdraw the needle 170 from the cannula 148. For example, a return motion of the coil spring after moving from the retracted state to the extended state may provide sufficient force to withdraw the needle 170 from the cannula 148.

Once the insert structure 166 has been locked into place within the housing 104 and the needle-inserting device 144 has been removed from the housing 104, the cannula 148 may be connected in fluid-flow communication with a connection portion 130 of a second member (such as, but not limited to a reservoir housing 108), in a manner similar to the manner in which the first and second members 102 and 103 are connectable in the embodiment of FIGS. 7-12. More specifically, the housing 104 may form a receptacle (similar to the receptacle 110 described above for FIGS. 7-12) and may contain a septum 116 that functions as a first septum (similar to the first septum 116 of FIGS. 7-12).

Similar to the embodiment of FIGS. 7-12, the connection portion 130 in FIG. 7 also may also a second septum 136. In particular, the connection portion 130 may be inserted into the receptacle formed by the housing 104 to connect the interior of the reservoir housing 108 in fluid-flow communication with the cannula 148. The cannula 148 in FIG. 13 may include a sharp end 148a adjacent the septum 116. As the connection portion 130 is inserted into the housing 104, the connection portion may push the septum 116 against the sharp end 148a of the cannula 148 to cause the sharp end 148a of the cannula 148 to pierce the septum 116. Further insertion motion of the connection portion 130 into the housing 104 may cause the sharp end 148a of the cannula 148 to pierce the septum 136 in the connection portion 130, to form a flow path from or to the connection portion 130 through the cannula 148.

Figure 17:
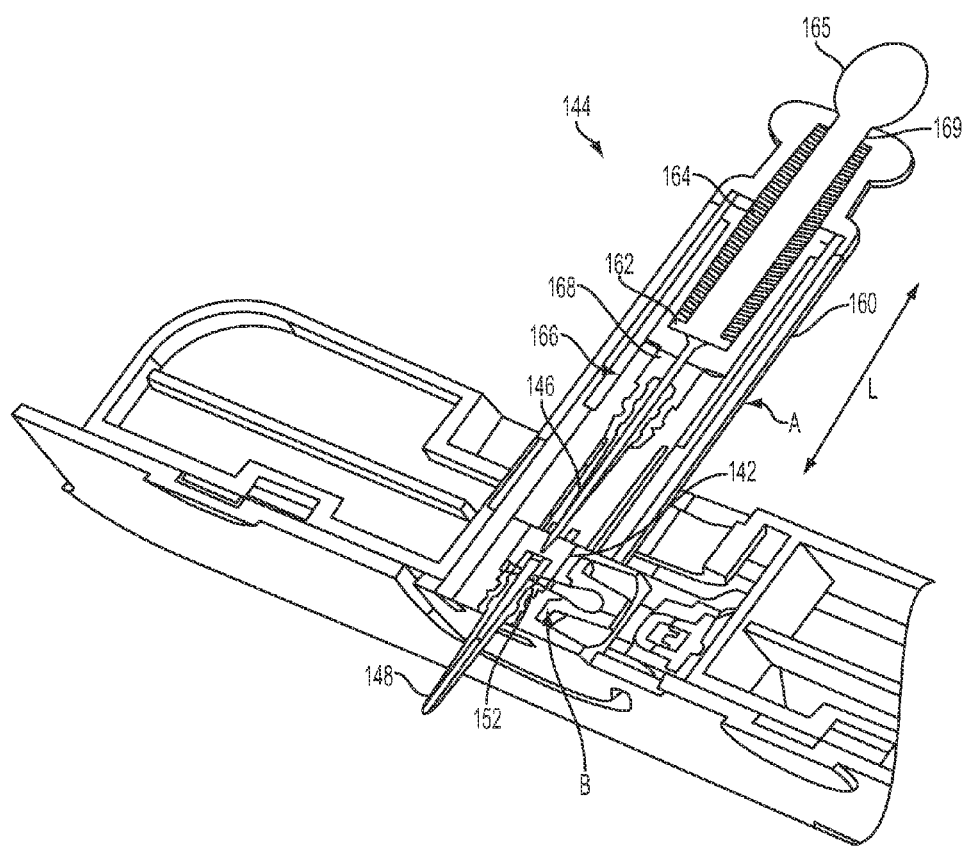
FIG. 17 illustrates a cross-section of a needle-inserting device in accordance with an embodiment of the present invention.

FIG. 17 illustrates a needle-inserting device 144 according to an embodiment of the present invention. Components in FIG. 17 are identified by reference numbers that are the same reference numbers used in FIGS. 7-16 for components having similar structure and function. Similar to the embodiments of FIGS. 7-16, the needle-inserting device 144 may also include a plunger 162, a bias member 164, an insert structure 166, a needle 146, and a cannula 148.

The needle-inserting device 144 in FIG. 17 may include a housing 160 that is securable to the base 106 in any suitable manner, such as, but not limited to the manners of connecting an inserting device 144 to the housing 105 discussed above with respect to the embodiments of FIGS. 7-16. As shown in FIG. 17, the housing 160 may contain an internal chamber having a longitudinal dimension L. The moveable plunger 162 may be located at least partially within the housing 160 and may be moveable along the longitudinal dimension L to move the insert structure 166, the needle 146, and the cannula 148, between at least a retracted position (A in FIG. 17) to an extended position (B in FIG. 17).

The bias member 164, which may be, but is not limited to, a coil spring may be arranged within the housing 160 to impart a bias force on the plunger 162 when the plunger 162 is in a retracted position (A in FIG. 17) to urge the plunger 162 along the longitudinal dimension L and move the insert structure 166, the needle 146, and the cannula 148 toward the extended position (B in FIG. 17). In other embodiments, the bias member 164 may be provided by other suitable means for imparting a bias force on the plunger 162. These may include, but are not limited to, other types of springs, pressurized fluid within the chamber, a collapsible skirt structure with a natural or built-in spring force, chemical, or substance that expands upon contact with another chemical or substance or upon application of energy from an energy source such as a heat, laser, or other radiation source, or the like.

A locking mechanism (not shown) may be provided, such as, but not limited to, a manually moveable projection, lever, slider, or the like, that may be connected to or extends through the housing 160 and engages the plunger 162 (or other structure holding the plunger 162) in a releasable manner to selectively hold the plunger 162 in its retracted state (A in FIG. 17) against the bias force of the bias member 164 and to allow a user to selectively release the plunger 162 to move in the longitudinal direction L under the force of the bias member 164.

In some embodiments, the locking mechanism (not shown) may be a tab 165 connected to an end of the plunger 162. At least a portion of the tab 165 and/or the plunger 162 may extend out the housing 160 through an opening 169 in the housing 160. In some embodiments, the tab 165 may be integral to the plunger 162, while in other embodiments, the tab 165 may be connected to the plunger 162. The tab 165 may be sized and/or configured such that the tab 165 cannot fit through the opening 169 in the housing 160 and into the internal chamber of the housing 160. The tab 165 illustrated in FIG. 17 has a diameter slightly larger than a diameter of the opening 169 in the housing 160. As such, the tab 165 is able to selectively hold the plunger 162 in its retracted state (A in FIG. 17) against the bias force of the bias member 164 and to allow a user to selectively release the plunger 162 to move in the longitudinal direction L under the force of the bias member 164.

To operate the needle-inserting device 144, the user, for example, may apply force to the tab 165 relative to the plunger 162 and/or housing 160 to break the tab 165 away from the plunger 162. This may allow the bias force provided by the bias member 164 to urge the plunger 162 along the longitudinal dimension L to move the insert structure 166, the needle 146, and the cannula 148 toward the extended position (B in FIG. 17). Although the tab 165 may be configured to be broken away from the plunger 162 and/or housing 160 to free the plunger 162 in some embodiments, alternatively or additionally, the tab 165 may be configured to be removable in various ways, such as, but not limited to, by twisting off the tab 165 or pulling off the tab 165.

In other embodiments, the tab 165 and/or the plunger 162 may be configured such that the tab 165 can be turned or twisted in a manner to allow the tab 165 to align with and fit through the opening 169 in the housing 160. In further embodiments, the tab 165 may be made of a rigid material having a slight flexibility. In such embodiments, the tab 165 may be able to hold the plunger 162 in its retracted state (A in FIG. 17). However, if a user applies a small amount of force or pressure to squeeze or otherwise compress the tab 165 to a size of comparable size and shape as (or smaller than) the opening 169 in the housing 160, the tab 165 and the plunger 165 may be able to advance within the internal chamber of the housing 160 to move the needle 146, the cannula 148, and the insert structure 166 to the extended position (B in FIG. 17).

In some embodiments, once the plunger 162 is advanced to the extended position (B in FIG. 17), the insert structure 166 may connect to the base housing 104 (FIG. 13) through use of any suitable connection structure. In particular embodiments, the insert structure 166 may have a member 168 and the housing 104 may include one or more flexible pawls, protrusions, indentations, or the like, for engaging and receiving one or more corresponding pawls, protrusions, indentations, or the like, on the other of the housing 104 and the insert structure 166 to provide a suitable connection structure. Alternatively or in addition, the connection structure may include adhesive material or other suitable connectors. FIG. 17 shows the insert structure 166 in the extended position (B), and locked into the housing 104 (e.g., after insertion by the inserting device 144 and after removal of the inserting device 144 from the housing 104).

The cannula 148 may have a connection channel 152 provided in fluid-flow communication with a central longitudinal channel of the cannula 148. The connection channel 152 may be provided, along the longitudinal length of the cannula 148, and aligned with a fluid channel in fluid communication with a reservoir (not shown) containing fluidic media when the needle 146 and the cannula 148 have been moved to the extended state (B in FIG. 17) by the needle-inserting device 144. In this manner, upon the cannula 148 being moved to the extended state, the central longitudinal channel of the cannula 148 may be arranged in fluid flow communication with the reservoir (not shown), the fluid channel, and the connection channel 152.

Figure 18A:
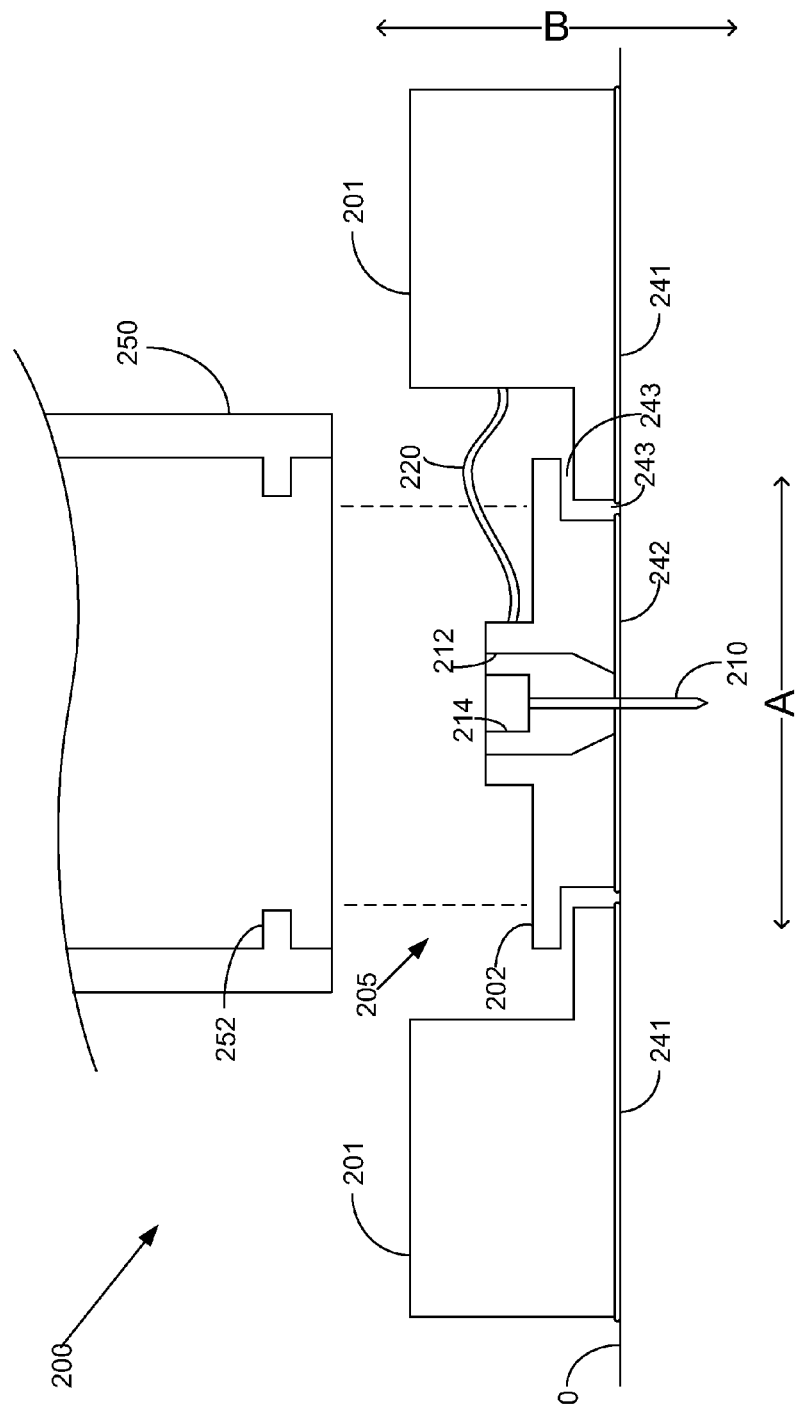
FIG. 18A illustrates a cross-section of a medical device in accordance with an embodiment of the present invention.

FIGS. 18A and 18B illustrate a medical device 200 in accordance with an embodiment of the present invention. The medical device 200 may include, but is not limited to, a base 201, a structure 202, and at least one of a cannula 210 and a needle (not shown). The base 201 may be made of any suitably rigid material, including, but not limited to plastic, metal, ceramic, composite material, or the like. In other embodiments, the base 201 may be made of any other suitable material as may be required.

The structure 202 may be connected to and supported by the base 201. The structure 202 and the base 201 may be configured for relative movement to each other. For example, the structure 202 and the base 201 may be configured such that the structure 202 remains substantially still and the base 201 is moveable in a case where the medical device 200 is moved, for instance.

In some embodiments, the base 201 may have an interior area 205 containing the structure 202. The base 201 may be removably attachable to a user-patient. For example, the base 201 may have an adhesive layer 241 having a certain adhesion strength. The adhesive layer 241 may be for adhering the base 201 to skin 0 or clothing of the user-patient to affix or otherwise secure the base 201 to the user-patient.

In other embodiments, the structure 202 may be located at any suitable location on or along the base 201 that allows the structure 202 and the base 201 to be connected and allow for relative movement between the structure 202 and the base 201. For example, the base 201 may have a recess (not shown) or alcove on an edge of the base 201 with the structure 202 positioned at least partially in the recess (not shown). In yet other embodiments, the structure 202 may be located sufficiently near the base 201 to allow the structure 202 and the base 201 to be connected and allow for relative movement between the structure 202 and the base 201. For example, the structure 202 may be positioned adjacent to an edge of the base 201. In further embodiments, a housing (not shown) may be adapted to install to, cover, or otherwise receive the structure 202 and the base 201.

For example, the housing (not shown) may be configured to be attachable to one or more of the structure 202 and the base 201. The housing (not shown) may be, for example, installed to the structure 202 and/or the base 201 prior to one or both of the structure 202 and the base 201 being affixed to the user-patient. In some embodiments, the housing (not shown) may be, for example, installed to the structure 202 and/or the base 201 after one or both of the structure 202 and the base 201 are affixed to the user-patient.

The structure 202 may include a cannula 210 and/or a needle (not shown), which may be inserted into a user-patient for conveying fluidic media to or from the user-patient. The structure 202 may be removably attachable to the user-patient. For example, the structure 202 may have an adhesive layer 242 having a certain adhesion strength. The adhesive layer 242 may be for adhering the structure 202 to skin 0 or clothing of the user-patient to affix or otherwise secure the structure 202 to the user-patient.

In some embodiments, the adhesive layer 242 of the structure 202 may have an adhesion strength greater than an adhesion strength of the adhesive layer 241 of the base 201. In some embodiments, employing an adhesive layer 242 with the structure 202 with a greater adhesion strength may allow for the structure 202 and the cannula 210 and/or needle (not shown) to remain relatively still while attached to the skin 0 of the user-patient.

In some embodiments, a first portion of the adhesive layer 242 of the structure 202 may have an adhesion strength greater than an adhesion strength of a second portion of the adhesive layer 242 of the structure 202. For example, the first portion of the adhesive layer 242 may be along a periphery of the structure 202, which may allow for stronger adhesion to the user-patient along the periphery or edges of the structure 202. As another example, the first portion of the adhesive layer 242 of the structure 202 may be near or adjacent an insertion site, such as where the cannula 210 and/or needle (not shown) pierce the skin of the user-patient, which may allow for stronger adhesion to the user-patient at the insertion site.

In some embodiments, a first portion of the adhesive layer 241 of the base 201 may have an adhesion strength greater than an adhesion strength of a second portion of the adhesive layer 241 of the base 201. For example, the first portion of the adhesive layer 241 may be along a periphery of the base 201, which may allow for stronger adhesion to the user-patient along the periphery or edges of the base 201.

The structure 202 may include a channel 214 extending at least partially through the structure 202. The channel 214 may allow a needle (not shown) and/or a cannula (such as 210) to pass through the channel 214 when the needle and/or cannula are inserted into the skin 0 of the user-patient, for example, with a needle insertion device 250 (or 144 as discussed with respect to FIGS. 7-17), or as described in various examples of suitable structure for needle-inserting devices as described in U.S. patent application Ser. No. 11/645,435, filed Dec. 26, 2006, entitled "Infusion Medium Delivery system, Device And Method With Needle Inserter And Needle Inserter Device And Method," which is assigned to the assignee of the present invention and is incorporated herein by reference, in its entirety.

In addition, the channel 214 may be aligned with the cannula 210 in a case where the cannula 210 is already inserted into the skin 0 of the user-patient. The channel 214 may be in fluid communication with a fluid connection 220, which may be in fluid communication with a reservoir (not shown) containing fluidic media. Thus, fluidic media may be able to flow from the reservoir (not shown) through the fluid connection 220 into the channel 214 and the cannula 210 to the user-patient.

In some embodiments, the fluid connection 220 may be made of a flexible tubing and may be made of any suitable material for delivering fluidic media from the reservoir (not shown) to the user-patient.

The structure 202 illustrated in FIG. 18A may be separate and apart from the base 201. There may be a space 243 located between the structure 202 and the base 201 to allow for some movement—in an axial direction, a lateral direction, or both—of the base 201 relative to the structure 202. For example, in a case where the base 201 and the structure 202 are affixed to the skin 0 of the user-patient and the base 201 is moved or shifted, the base 201 can move laterally and/or latitudinally along the space 243 provided between the base 201 and the structure 202, as illustrated in FIG. 18B. This may allow the structure 202 attached to the skin 0 of the user-patient and the cannula 210 and/or needle (not shown) inserted into the skin 0 of the user-patient to remain relatively motionless to prevent injury to the user-patient or damage to the medical device 200.

With reference to FIGS. 18A and 18B, in other embodiments, the structure 202 may be at least partially connected to the base 201. For example, one side of the structure 202 and one side of the base 201 may be connected or otherwise integral to one another. In further embodiments, the structure 202 and the base 201 may be connected by a living hinge (not shown) or the like, which may be formed for example by injection molding with at least one of the base 201 and the structure 202. In further embodiments, the living hinge (not shown) may be adapted or configured in any suitable manner to release a needle-inserting device 250 (discussed later) from the base 201.

In yet other embodiments, the medical device 200 may include a flexible connection (e.g., a living hinge) between the structure 202 and the base 201. In further embodiments, the flexible connection may be adapted or configured in any suitable manner to release a needle-inserting device 250 (discussed later) from the base 201. In some embodiments, the medical device 200 may include a bias member (not shown), such as a spring, or the like, located for example in the space 243 provided between the base 201 and the structure 202. In such embodiments, the bias member (not shown) may allow for some movement of the base 201 relative to the structure 202 while allowing the structure 202 to remain relatively motionless. In further embodiments, the bias member may be adapted or configured in any suitable manner to release a needle-inserting device 250 (discussed later) from the base 201.

In some embodiments, at least one of the structure 202, the cannula 210, and the needle (not shown) may be placed or otherwise installed to the base 201, for example, in the interior area 205 of the base 201, with a needle-inserting device 250, such as a needle-inserting device as disclosed with respect to FIGS. 7-17 or other examples of suitable needle-inserting devices as described in U.S. patent application Ser. No. 11/645,435, filed Dec. 26, 2006, entitled "Infusion Medium Delivery system, Device And Method With Needle Inserter And Needle Inserter Device And Method," which is assigned to the assignee of the present invention and is incorporated herein by reference, in its entirety. In further embodiments, the needle-inserting device 250 may be configured to receive at least a portion of the structure 202, for example with tabs 252, or the like.

In various embodiments, the structure 202 may be a sensor (not shown) for sensing a parameter (e.g., physiological parameter) of the user-patient, such as glucose concentration, temperature, or the like. Thus, in some embodiments, the sensor (not shown) may be arranged relative to the base 201 for movement therebetween. The sensor (not shown) may be configured to communicate (e.g., wired electrical communication, wireless electrical communication) with at least one of the base 201 and/or the medical device 200.

In other embodiments, the sensor (not shown) may be arranged relative to the structure 202. For example, the sensor (not shown) may be disposed within the structure 202 or on an edge of the structure 202. The sensor (not shown) may be operatively connected to (e.g., wired electrical connection, wireless connection) and supported by the structure 202. Any of the base 201, the structure 202, and the sensor (not shown) may be configured for relative movement to each other. In some embodiments, any of the base 201, the structure 202, and the sensor (not shown) may be configured such that the sensor (not shown) remains substantially still and the structure 202 and/or the base 201 is moveable in a case where the medical device 200 is moved, for instance. In various embodiments, the sensor (not shown) may be placed or otherwise installed to the base 201 and/or structure 202 with an insertion device adapted to place or otherwise install the sensor (not shown) to the base 201 and/or structure 202, similar to needle-inserting device 250.

FIGS. 19A and 19B illustrate a medical device 300 according to an embodiment of the present invention. The medical device 300 may include a base 301 and a needle-inserting device 350. The needle-inserting device 350, may be a needle-inserting device as disclosed with respect to FIGS. 7-18B or other various examples of suitable needle-inserting devices as described in U.S. patent application Ser. No. 11/645,435, filed Dec. 26, 2006, entitled "Infusion Medium Delivery system, Device And Method With Needle Inserter And Needle Inserter Device And Method," which is assigned to the assignee of the present invention and is incorporated herein by reference, in its entirety.

The needle-inserting device 350 may include at least one of a needle 355 or cannula (not shown). The base 301 may include a top portion 302. The base 301 and the top portion 302 may have an opening 305 for inserting at least a portion of the needle-inserting device 350, for example to pierce skin 0 of a user-patient of an injection site 315. The opening 305 may be directly above the injection site 315 on the skin 0 of the user-patient, such that the opening 305 is in vertical alignment with the injection site 315 on the skin 0 of the user-patient. In other embodiments, such as the embodiment shown in FIG. 20 the opening 306 may be angled relative to the injection site 315 on the skin 0 of the user-patient, such that the opening 306 is disaligned with the injection site 315 on the skin 0 of the user-patient. In such embodiments, the needle-inserting device 350 can be inserted, for example, at an angle less than (or greater than) 90 degrees through the opening 306.

With reference to FIGS. 19A and 19B, in some embodiments, the top portion 302 may include a magnifying area 310. The magnifying area 310 may magnify or otherwise increase visibility of the injection site 315. This may allow, for example, the user-patient to accurately insert the needle 355 of the needle-inserting device 350 into his or her skin 0. As such, the user-patient may look through the magnifying area 310 to see the injection site 315 on his or her skin 0 and accordingly insert the needle-inserting device 350 into the opening 305 and pierce the skin 0 with the needle 355. The user-patient may look into the magnifying area 310 at any time before, during, and after inserting the needle-inserting device 350 into the opening 305. Likewise, the user-patient may look into the magnifying area 310 to accurately place the base 301 at a specific location on his or her skin 0.

Throughout various embodiments, the magnifying area 310 may be located at any suitable allow that would allow the user-patient to view the injection site 315. For example, the magnifying area 310 may be located directly above the injection site 315. In other embodiments, the magnifying area 310 may be offset from the injection site 315. In such embodiments, the user-patient may view the injection site 315 through the magnifying area 310 at an angle. In yet other embodiments, the magnifying area 310 may be located on the needle-inserting device 350, for example at a bottom end, a top end, or a side of the needle-inserting device 350. In some of those embodiments, the magnifying area 310 of the needle-inserting device 350 may be at least partially inserted into the opening 305, in which case the user-patient may look into the opening 305 to view the injection site 315 through the magnifying area 310 located on the needle-inserting device 350.

The embodiments disclosed herein are to be considered in all respects as illustrative, and not restrictive of the invention. The present invention is in no way limited to the embodiments described above. Various modifications and changes may be made to the embodiments without departing from the spirit and scope of the invention. The scope of the invention is indicated by the attached claims, rather than the embodiments. Various modifications and changes that come within the meaning and range of equivalency of the claims are intended to be within the scope of the invention.

What is claimed is:

1. A needle-inserting device comprising:
   a housing having a flexible portion, an internal chamber, a longitudinal dimension, and an internal surface having an angled, ramped or wedge-shaped portion;
   a plunger arranged for movement within the internal chamber, in the direction of the longitudinal dimension of the housing, from a first plunger position to a second plunger position;
   a bias mechanism for imparting a bias force on the plunger when the plunger is in the first plunger position, wherein the bias force is directed toward the second plunger position; and
   a needle connected to the plunger for movement with the plunger; and
   a tab connected to or integral with and the plunger and carried by the plunger, the tab having a tab end configured to retain the plunger in the first plunger position, the tab end moveable relative to the housing;
   an insert structure arranged for movement within the internal chamber of the housing with movement of the plunger from the first plunger position to the second plunger position, the insert structure including a body through which the needle extends, wherein at least one of the plunger or the body of the insert structure is arranged to engage the angled, ramped or wedge-shaped portion of the housing and outwardly flex the flexible portion of the housing upon the insert structure being moved as the plunger moves from the first plunger position to the second plunger position;
   wherein upon movement of the tab end, the plunger is released from being retained in the first plunger position by the tab end and moves with the tab end, relative to the housing, in the direction of the longitudinal dimension of the housing from the first plunger position to the second plunger position under the bias force imparted by the bias mechanism to move the needle to an insert position and outwardly flex the flexible portion of the housing.

2. The needle-inserting device of claim 1, wherein the bias mechanism comprises a chemical substance that expands upon application of another substance or energy from an energy source.

3. The needle-inserting device of claim 1, wherein the tab end is integral with the plunger, but fractures to break off from the plunger upon being moved to release the plunger from being retained in the first plunger position.

4. The needle-inserting device of claim 1, wherein the tab end is located outside of the internal chamber of the housing when the plunger is retained in the first plunger position, and the entire plunger is arranged within the internal chamber of the housing when the plunger is retained in the first plunger position.

5. The needle-inserting device of claim 1, wherein the tab end is located outside of the internal chamber of the housing when the plunger is retained in the first plunger position, the entire plunger and all portions of the tab other than the tab end are arranged within the internal chamber of the housing when the plunger is retained in the first plunger position, and the entire tab end is moveable relative to the housing to detach from the plunger and all portions of the tab arranged within the internal chamber of the housing.

6. The needle-inserting device of claim 1, wherein all portions of the tab other than the tab end are arranged within the internal chamber of the housing when the plunger is retained in the first plunger position, and wherein the entire tab end is moveable relative to the housing to detach from all portions of the tab arranged within the internal chamber of the housing.

7. The needle-inserting device of claim 1, wherein at least a portion of the needle is adapted to pierce skin of a user as the plunger moves from the first plunger position to the second plunger position to move the needle to the insert position.

8. The needle-inserting device of claim 1, the housing having an opening that opens to the internal chamber, the opening having a width dimension; the tab end having a width dimension larger than the width dimension of the opening.

9. The needle-inserting device of claim 8, the tab end configured to be one of rotatable and twistable to fit within the opening of the housing to release the plunger from being retained in the first plunger position.

10. The needle-inserting device of claim 8, the tab end configured to be compressible to fit within the opening of the housing to release the plunger from being retained in the first plunger position.

11. The needle-inserting device of claim 8, wherein the tab end is located on one side of the opening of the housing prior to the tab end being moved to release the plunger, the tab end passing through the opening of the housing when the tab end is moved to release the plunger head from being retained in the first plunger position.

12. The needle-inserting device of claim 1, the device further comprising:
a hollow cannula having a hollow interior and arranged with the needle extending through the hollow interior;
wherein upon movement of the tab end, the plunger is free to move from the first plunger position to the second plunger position under the bias force imparted by the bias mechanism to move the hollow cannula to a cannula insert position.

13. The needle-inserting device of claim 12, wherein at least a portion of the cannula is adapted to pierce skin of a user as the plunger moves from the first plunger position to the second plunger position to move the cannula to the cannula insert position.

14. The needle-inserting device of claim 1, the device further comprising:
an insert structure arranged for movement within the internal chamber of the housing with movement of the plunger from the first plunger position to the second plunger position, the insert structure including a body through which the needle extends;
the housing having at least one slot or groove;
the body of the insert structure including a shaped portion configured to engage the at least one slot or groove upon the insert structure being moved as the plunger moves from the first plunger position to the second plunger position.

15. The needle-inserting device of claim 14,
the housing having a flexible portion in the vicinity of the at least one slot or groove; and
the body of the insert structure arranged to engage and outwardly flex the flexible portion of the housing upon the insert structure being moved as the plunger moves from the first plunger position to the second plunger position.

16. The needle-inserting device of claim 1, the device further comprising:
an insert structure arranged for movement within the internal chamber of the housing with movement of the plunger from the first plunger position to the second plunger position, the insert structure including a body through which the needle extends;
the insert structure having a fluid channel, the fluid channel operatively connectable to a reservoir when the insert structure moves with the plunger from the first plunger position to the second plunger position.

17. The needle-inserting device of claim 16, the device further comprising:
a hollow cannula having a hollow interior and arranged with the needle extending through the hollow interior;
wherein upon movement of the tab end, the plunger is free to move from the first plunger position to the second plunger position under the bias force imparted by the bias mechanism to move the hollow cannula to an insert position; and
wherein the fluid channel is in fluid communication with the hollow interior of the cannula upon the insert structure being moved with the plunger from the first plunger position to the second plunger position.

18. A medical device having the needle-inserting device of claim 1, the medical device further comprising:
a medical monitoring or treatment device configured to provide a monitoring or treatment operation on a user, the medical monitoring or treatment device operable with the needle of the needle-inserting device;
a medical device housing adapted to be secured to the user for supporting the medical monitoring or treatment device during operation of the medical monitoring or treatment device;
a magnifying material arranged on the medical device housing for increasing visibility of an injection site on skin of the user when piercing the skin of the user with the needle of the needle-inserting device.

19. The medical device of claim 18,
the medical device housing having an opening for inserting at least a portion of the needle of the needle-inserting device;
wherein the opening is in vertical alignment with the injection site.

20. The medical device of claim 18,
the medical device housing having an opening for inserting at least a portion of the needle of the needle-inserting device;
wherein the opening is disaligned with the injection site.

21. The medical device of claim 18,
wherein at least a portion of the magnifying area is located above the injection site.

22. The medical device of claim 18,
wherein the magnifying area is laterally offset to the injection site.

23. A medical device having the needle-inserting device of claim 1, the medical device further comprising:
a medical monitoring or treatment device configured to provide a monitoring or treatment operation on a user;
a base adapted to be secured to the user during operation of the medical monitoring or treatment device;
a structure adapted to be secured to the user during operation of the medical monitoring or treatment device, the structure connected to and supported by the base, the structure having a body, the structure and the base configured for relative movement there between; and
a cannula extending through the body of the structure during operation of the medical monitoring or treatment device, the cannula for inserting into the user with the needle of the needle-inserting device as the plunger of the needle-inserting device is moved under the bias force of the bias mechanism, to the second plunger position, the cannula for remaining in the user during operation of the medical monitoring or treatment device.

24. The medical device of claim 23, the structure arranged to be separate and apart from the base.

25. The medical device of claim 23, the structure operatively connected to the base.

26. The medical device of claim 23, the device further comprising:
a bias member provided between the base and the structure.

27. The medical device of claim 23,
the base having an interior chamber;
wherein the cannula is supported within the interior chamber of the base.

28. The medical device of claim 23,
the base having an interior chamber;
wherein the structure is supported within the interior chamber of the base.

29. The medical device of claim 23, the device further comprising:
an adhesive material provided on at least a portion of the structure and at least a portion of the base for securing the at least one of the base and the structure to the user, the adhesive material having a different adhesion strength on the structure than on the base.

30. The medical device of claim 23, the device further comprising:
an adhesive material provided on at least a first portion of the structure and at least a second portion of the structure for securing the structure to the user, the adhesive material having a different adhesion strength on the first portion than on the second portion.

31. The medical device of claim 23, the device further comprising:
an adhesive material provided on at least a first portion of the base and at least a second portion of the base for securing the base to the user, the adhesive material having a different adhesion strength on the first portion than on the second portion.

32. The medical device of claim 23, wherein the structure comprises a sensor for sensing a parameter of the user during operation of the medical monitoring or treatment device.

33. The medical device of claim 23, the device further comprising:
a sensor for sensing a parameter of the user during operation of the medical monitoring or treatment device, the sensor operatively connected to and supported by the structure.

34. The medical device of claim 23, the device further comprising:
a flexible connection connecting the base and the structure.

35. The medical device of claim 34,
at least one of the base, the structure, and the cannula placeable by the needle-inserting device;
the flexible connection adapted to release the needle-inserting device after placement of the at least one of the base, the structure, and the cannula.

36. The medical device of claim 34,
wherein the flexible connection comprises a living hinge connecting the base and the structure.

37. The medical device of claim 23, the device further comprising:
a fluid connection in fluid communication with the cannula and a reservoir containing fluidic media.

38. The medical device of claim 37, wherein the fluid connection comprises a flexible tubing.

39. The medical device of claim 23,
wherein the base has a base surface facing skin of the user during operation of the medical monitoring or treatment device;
wherein the base has an opening through the base surface; and
wherein the structure is supported at least partially within the opening.

40. The medical device of claim 39,
wherein the structure has an inserting surface facing skin of the user during operation of the medical monitoring or treatment device;
wherein an adhesive material provided on at least a portion of the base surface and at least a portion of the inserting surface for securing, the at least one of the base and the structure to the user, the adhesive material having a different adhesion strength on the structure than on the base.

41. A method of making a needle-inserting device, the method comprising:
providing a housing having a flexible portion, an internal chamber, a longitudinal dimension, and an internal surface having an angled, ramped or wedge-shaped portion;
arranging a plunger for movement within the internal chamber, in the direction of the longitudinal dimension of the housing, from a first plunger position to a second plunger position, the plunger having a tab end;
providing a bias mechanism for imparting a bias force on the plunger when the plunger is in the first plunger position, wherein the bias force is directed toward the second plunger position; and
locating a needle connected to the plunger, for movement with the plunger;
arranging an insert structure within the internal chamber of the housing, for movement with movement of the plunger from the first plunger position to the second plunger position, the insert structure including a body through which the needle extends, and arranging at least one of the plunger or the body of the insert structure to engage the angled, ramped or wedge-shaped portion of the housing and outwardly flex the flexible portion of the housing upon the insert structure being moved as the plunger moves from the first plunger position to the second plunger position; and
configuring the tab end of the plunger to retain the plunger in the first plunger position, the tab end moveable relative to the housing such that upon movement of the tab end relative to the housing, the plunger is released from being retained in the first plunger position by the tab end and moves with the tab end, relative to the housing, in the direction of the longitudinal dimension of the housing from the first plunger position to the second plunger position under the bias force imparted by the bias mechanism to move the needle to an insert position and outwardly flex the flexible portion of the housing.

42. The needle-inserting device of claim 41, wherein the tab end is fixed to and held by the plunger prior to the tab end being moved to release the plunger, and remains fixed to the plunger as the plunger moves from a first plunger position to a second plunger position.

43. The method of claim 41, further comprising:
providing an opening in the housing that opens to the internal chamber, the opening having a width dimension smaller than a width dimension of the tab end;
wherein arranging the plunger further comprises arranging the plunger with the tab end located on one side of the opening of the housing prior to the tab end being moved to release the plunger; and
wherein configuring the tab end further comprises configuring the tab end to pass through the opening of the housing when the tab end is moved to release the plunger head from being retained in the first plunger position.

44. The method of claim 43, wherein configuring the tab end to pass through the opening of the housing when the tab end is moved to release the plunger head comprises configuring the tab end to compress to a size to fit and pass through the opening of the housing to release the plunger head.

45. The method of claim 43, wherein configuring the tab end to pass through the opening of the housing when the tab end is moved to release the plunger head comprises configuring the tab end to rotate or twist to fit and pass through the opening of the housing to release the plunger head.

46. A needle-inserting device, comprising:
a housing having a flexible portion, an internal chamber, a longitudinal dimension, and an internal surface having an angled, ramped or wedge-shaped portion;
a plunger arranged for movement within the internal chamber, in the direction of the longitudinal dimension of the housing, from a first plunger position to a second plunger position;

a bias mechanism for imparting a bias force on the plunger when the plunger is in the first plunger position, wherein the bias force is directed toward the second plunger position; and a needle connected to the plunger for movement with the plunger; and a tab integral with the plunger, the tab having a tab end configured to retain the plunger in the first plunger position, the tab end moveable relative to the housing and configured to be broken off the plunger;

an insert structure arranged for movement within the internal chamber of the housing with movement of the plunger from the first plunger position to the second plunger position, the insert structure including a body through which the needle extends, wherein at least one of the plunger or the body of the insert structure is arranged to engage the angled, ramped or wedge-shaped portion of the housing and outwardly flex the flexible portion of the housing upon the insert structure being moved as the plunger moves from the first plunger position to the second plunger position;

wherein upon movement of the tab end to break off the plunger, the plunger is free to move from the first plunger position to the second plunger position under the bias force imparted by the bias mechanism to move the needle to an insert position.

47. The needle-inserting device of claim 46, wherein the tab end is fixed to and held by the plunger prior to the tab end being moved to release the plunger, and wherein the tab end is fractured and broken off from the plunger when it is moved to release the plunger.

\* \* \* \* \*